(12) United States Patent
Brimble et al.

(10) Patent No.: US 8,067,425 B2
(45) Date of Patent: *Nov. 29, 2011

(54) NEUROPROTECTIVE BICYCLIC COMPOUNDS AND METHODS FOR THEIR USE

(75) Inventors: Margaret Anne Brimble, Auckland (NZ); Jian Guan, Auckland (NZ); Frank Sieg, Auckland (NZ)

(73) Assignee: Neuren Pharmaceuticals Limited, Auckland (NZ)

( * ) Notice: Subject to any disclaimer, the term of this patent is extended or adjusted under 35 U.S.C. 154(b) by 397 days.

This patent is subject to a terminal disclaimer.

(21) Appl. No.: 10/570,395

(22) PCT Filed: Aug. 31, 2004

(86) PCT No.: PCT/US2004/028308
§ 371 (c)(1),
(2), (4) Date: Mar. 2, 2007

(87) PCT Pub. No.: WO2005/023815
PCT Pub. Date: Mar. 17, 2005

(65) Prior Publication Data
US 2007/0197511 A1  Aug. 23, 2007

Related U.S. Application Data

(60) Provisional application No. 60/499,956, filed on Sep. 3, 2003.

(51) Int. Cl.
*A61K 31/517* (2006.01)
(52) U.S. Cl. .................... 514/259.5; 544/282
(58) Field of Classification Search .............. 544/282
See application file for complete search history.

(56) References Cited

U.S. PATENT DOCUMENTS
6,147,051 A * 11/2000 Watanabe et al. .......... 514/11

FOREIGN PATENT DOCUMENTS
| WO | WO 99/40931 | | 8/1999 |
| WO | WO 03/039487 | * | 5/2003 |
| WO | WO 03/041655 | | 5/2003 |

OTHER PUBLICATIONS

West, Anthony R., Solid State Chemistry and its Applications, Wiley, New York, 1988, pp. 358 and 365.*
ISR and IPER of PCT/US04/028308, Aug. 31, 2004, Neuren Pharmaceuticals.
Prakash, K.R.C., et al., "Synthesis and Biological Activity of Novel Neuroprotective Diketopiperazines", Biorganic & Medicinal Chemistry, 2002 Elsevier Science Ltd.
Office Action dated Mar. 11, 2009 in U.S. Appl. No. 11/399,974.
IDS in U.S. Appl. No. 11/399,974 dated May 5, 2009, citing International Preliminary Report dated Apr. 23, 2009 in PCT/US2007/021744.
Reply to Office Action dated Jun. 16, 2009 in U.S. Appl. No. 11/399,974.
Office Action dated Sep. 25, 2009 in U.S. Appl. No. 11/399,974 citing.
Mann, et al., "Dopaminergic neurotransmitter systems in Alzheimer's disease and in Down's syndrome at middle age", Journal of Neurology, Neurosurgery and Psychiatry 1987; 50:341-344.
Zarkovic, "4-Hydroxynonenal and neurodegenerative diseases", Molecular Aspects of Medicine 24 (2003) 293-303.
Kostic, "Midbrain Dopaminergic Neuronal Degeneration in a Transgenic Mouse Model of Familial Amyotrophic Lateral Sclerosis", American Neurological Association 1997, 497-504.
Guttman, Mark, "Current concepts in the diagnosis and management of Parkinson's disease", Canadian Medical Association 2003, 293-301.
Strategy for the Synthesis of Non-Proteinogenic Dipeptides, Liebigs Ann.Chem. 1988, 1025-1031; VCH Verlagsgesellachaft mbH, D-6940 Weinheim, 1988.
Cerebral Blood Flow & Metabolism, 23:342-354, 2003, The International Society for Cerebral Blood Flow and Metabolism, Lippincott Williams & Wilkins, Inc., Philadelphia.

* cited by examiner

*Primary Examiner* — James O Wilson
*Assistant Examiner* — Brian McDowell
(74) *Attorney, Agent, or Firm* — D. Benjamin Borson; Borson Law Group, PC

(57) ABSTRACT

Embodiments of this invention provide novel cyclic compounds structurally related to diketopiperazines and methods for their therapeutic use. Such compounds are neuroprotective and have utility as therapeutic agents for treatment of diseases, injuries and other conditions characterized by neuronal degeneration and/or death. Compounds are also useful for manufacture of medicaments useful for treatment of such conditions.

3 Claims, 4 Drawing Sheets

NEUROPROTECTIVE BICYCLIC COMPOUNDS AND METHODS FOR THEIR USE

RELATED APPLICATION

This application is a 371 National Phase Application of PCT/US04/28308, filed Aug. 31, 2004, which claims priority to U.S. Provisional Patent Application Ser. No. 60/499,956, filed Sep. 3, 2003, Margaret Anne Brimble, Jian Guan and Frank Sieg, inventors, titled "Neuroprotectdive Bicyclic Compounds and Methods for Their Use", each application incorporated herein fully by reference.

FIELD OF THE INVENTION

The present invention relates to novel bicyclic compounds structurally related to diketopiperazines and methods for their therapeutic use. In particular, this invention relates to the neuroprotective activity of such compounds. More particularly, this invention relates to the use of these compounds and pharmaceutical compositions thereof in the treatment of diseases and conditions characterised by neuronal degeneration and/or death.

BACKGROUND

Degeneration and/or death of cells in the nervous system are major factors in many diseases and medical conditions. Such diseases and conditions include traumatic brain and spinal cord injuries, stroke, neural perfusion secondary to cardiac arterial bypass graft surgery (CABG), Parkinson's disease, Alzheimer's disease, multiple sclerosis, amyotrophic lateral sclerosis and other neurodegenerative diseases. It is of interest to prevent or decrease such cell death and degeneration.

Certain compounds are useful as neuroprotective agents. One such compound is insulin-like growth factor 1 (IGF-1) (Scheepens et al., WO00/13650). IGF-1 is a naturally occurring peptide that can decrease the binding of glutamate to the glutamate receptors of neurons (Bourguinon, U.S. Pat. No. 5,804,550). IGF-1 can also decrease neuronal degradation caused by damage and disease. IGF-1 is cleaved by proteolysis in vivo to give $des_{1-3}$ IGF-1 and the N-terminal tripeptide Gly-Pro-Glu (GPE). GPE and analogues have been found to be neuroprotective (Gluckinan et al., U.S. Pat. No. 6,187,906 incorporated herein by reference).

However, such peptides are far from ideal for the treatment of neural death and degeneration especially as they are rapidly metabolised in vivo. There is a need for compounds that provide neuroprotective and neuroregenerative properties and are more metabolically stable especially as regards resistance to proteases.

A derivative of GPE; cyclic Pro-Gly ("cPG"), a diketopiperazine, has been shown to be neuroprotective and neuroregenerative. cPG was found to prevent toxic neural degeneration and cell death and to promote neurite outgrowth in neurons (Guan et al., PCT/US02/36235 incorporated herein by reference). Diketopiperazine analogues of thyrotropin-releasing hormone (TRH) are known to be neuroprotective (Kozikowski et al. WO99/40931).

SUMMARY

Embodiments of this invention include novel diketopiperazines that are structurally related to cPG.

One aspect of this invention provides novel cyclic compounds having the structural formulas and substitutents described below.

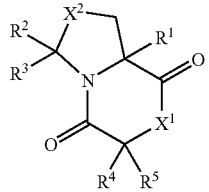

Formula 1

In some aspects, compounds of Formula 1 include substitutents where:

$X^1$ is selected from the group consisting of NR', O and S;
$X^2$ is selected from the group consisting of $CH_2$, NR', O and S;
$R^1$, $R^2$, $R^3$, $R^4$ and $R^5$ are independently selected from the group consisting of —H, —OR', —SR', —NR'R', —NO$_2$, —CN, —C(O)R', —C(O)OR', —C(O)NR'R', —CNR')NR'R', trihalomethyl, halogen, alkyl, substituted alkyl, heteroalkyl, substituted heteroalkyl, alkenyl, substituted alkenyl, alkynyl, substituted allynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^4$ and $R^5$ taken together are —$CH_2$—$(CH_2)_n$—$CH_2$— where n is an integer from 0-6;

or $R^2$ and $R^3$ taken together are —$CH_2$—$(CH_2)_n$—$CH_2$— where n is an integer from 0-6;

with the proviso that when $R^1$=methyl and $R^2$=$R^3$=$R^4$=H then $R^5 \neq$benzyl and;

when $R^1$=H, at least one of $R^2$ and $R^3 \neq$H.

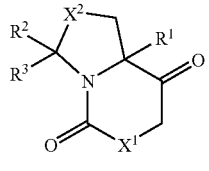

Formula 2

In other aspects, compounds of Formula 2 include substitutents where:

$X^1$ is selected from the group consisting of NR', O and S;
$X^2$ is selected from the group consisting of $CH_2$, NR', O and S;
$R^1$, $R^2$ and $R^3$ are independently selected from the group consisting of group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, alkenyl, substituted alkenyl, heteroalkyl, substituted heteroalkyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^2$ and $R^3$ taken together are —$CH_2$—$(CH_2)_n$—$CH_2$— where n is an integer from 0-6;

with the proviso that at least one R≠H,

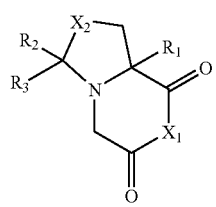

Formula 3

In additional aspects, compounds of Formula 3 include substitutents where:

$X^1$ is selected from the group consisting of NR', O and S;

$X^2$ is selected from the group consisting of CH$_2$, NR', O and S;

$R^1$, $R^2$ and $R^3$ are independently selected from the group consisting of group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^2$ and $R^3$ taken together are —CH$_2$—(CH$_2$)$_n$—CH$_2$— where n is an integer from 0-6.

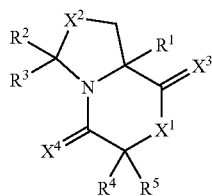

Formula 4

In further aspects, compounds of Formula 4 include substitutents where:

$X^1$, $X^3$, and $X^4$ are independently selected from the group consisting of S, O, and NH;

$X^2$ is selected from the group consisting of S, O, CH$_2$ and NH;

$R^1$, $R^2$, $R^3$, $R^4$ and W are independently selected from the group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^4$ and $R^5$ taken together are —CH$_2$—(CH$_2$)$_n$—CH$_2$— where n is an integer from 0-6;

or $R^2$ and $R^3$ taken together are —CH$_2$—(CH$_2$)$_n$—CH$_2$— where n is an integer from 0-6;

with the proviso that at least one R≠H and that both $X^3$ and $X^4$≠O.

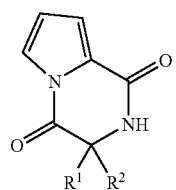

Formula 5

Additionally, other aspects, compounds of Formula 5 include substitutents where $R^1$ and $R^2$ are independently selected from the group consisting of group consisting of —H, —OR', —SR', —NR'R', —NO$_2$, —ON, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^1$ and $R^2$ taken together are —CH$_2$—(CH$_2$)$_n$—CH$_2$— where n is an integer from 0-6.

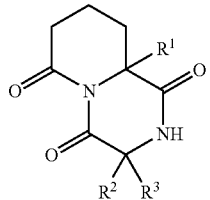

Formula 6

In other aspects, compounds of Formula 6 include substitutents where $R^1$, $R^2$ and $R^3$ are independently selected from the group consisting of group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^1$ and $R^3$ taken together are —CH$_2$—(CH$_2$)$_n$—CH$_2$— where n is an integer from 0-6.

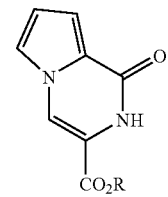

Formula 7

In yet other aspects, compounds of Formula 7 include substitutents where R is selected from the group consisting of alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl.

Other aspects of the invention provides pharmaceutically acceptable salts of the compounds described in Formulas 1-7.

In still other aspects, this invention provides pharmaceutical compositions comprising a pharmaceutically acceptable excipient and a therapeutically effective amount of at least one compound of this invention. These compositions find use as anti-apoptotic and anti-necrotic agents and for other conditions involving neural degeneration or injury.

In further aspects, this invention provides methods of treating an animal having a disease or injury capable of treatment by administration of a suitable compound of Formulas 1-7, comprising administration to that animal of at least one compound of this invention to decrease neurodegeneration caused by an injury or disease. In certain other aspects, this invention includes methods for treating an animal with a diketopiperazine of any of Formulas 1-7 in conjunction with at least one other conventional therapeutic agent for the disease being treated.

In yet further aspects, the animal to be treated is a human.

In still further aspects, this invention provides methods of synthesizing, formulating and preparing pharmaceutical preparations comprising compounds of Formulas 1-7 of this invention.

BRIEF DESCRIPTION OF THE DRAWINGS

This invention is described with reference to specific embodiments thereof. Other aspects of this invention can be appreciated with reference to the drawings, in which.

DETAILED DESCRIPTION

Definitions

Figure 1:
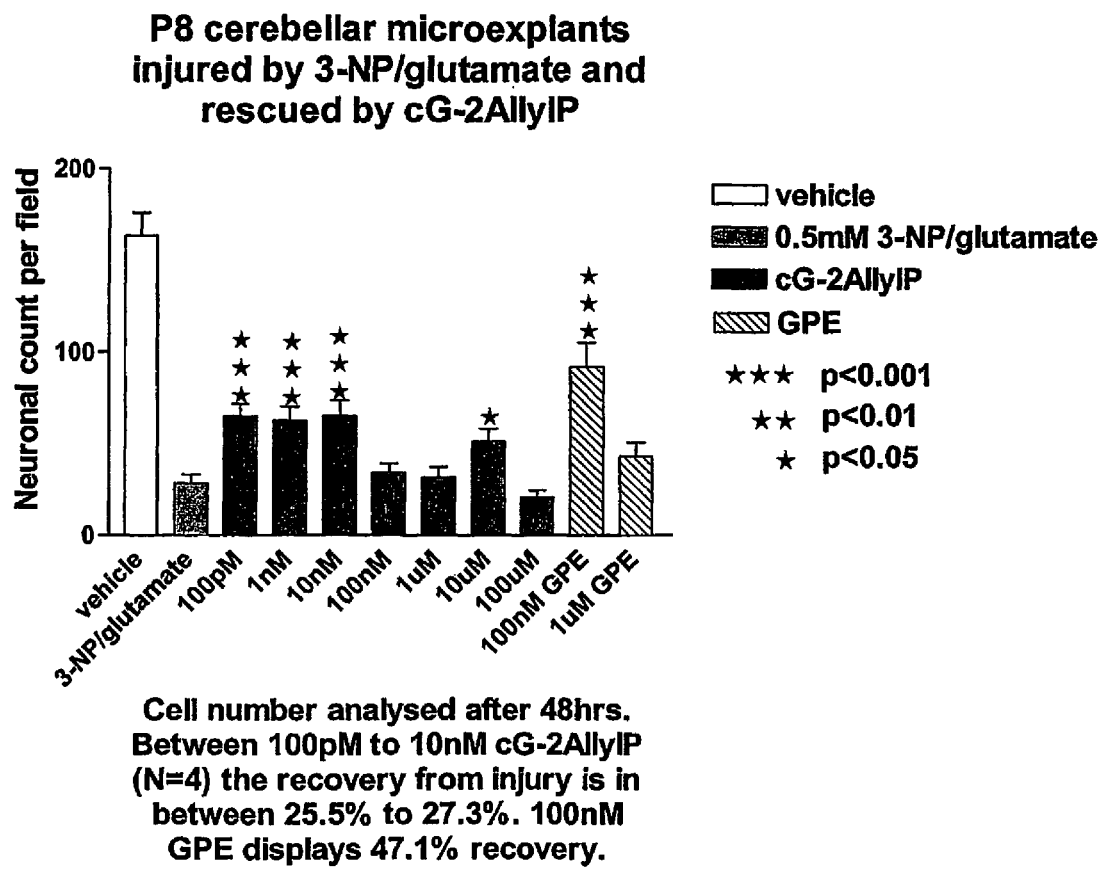
FIG. 1 is a graph showing effects of cyclic G-2allylP on neuronal survival in animals following excitotoxic oxidative stress.

"Alkenyl" refers to an unsaturated branched, straight chain or cyclic hydrocarbon radical having at least one carbon-carbon double bond. The radical may be in either the cis or trans conformation about the double bond(s). Exemplary alkenyl groups include allyl, ethenyl, propenyl, isopropenyl, butenyl, isobutenyl, cyclopentenyl and the like. In some embodiments the alkenyl groups are $(C_2-C_6)$ alkenyl, and in other embodiments, allyl can be particularly useful.

"Alkyl" refers to a saturated branched, straight chain or cyclic hydrocarbon radical. Exemplary alkyl groups include methyl, ethyl, isopropyl, cyclopropyl, tert-butyl, cyclopropylmethyl, hexyl and the like. In some embodiments the alkyl groups are $(C_1-C_6)$ alkyl.

"Alkynyl" refers to an unsaturated branched, straight chain or cyclic hydrocarbon radical having at least one carbon-carbon triple bond. Exemplary alkynyl groups include ethynyl, propynyl, butynyl, isobutynyl and the like. In some embodiments the alkynyl group is $(C_2-C_6)$ alkynyl.

"Aryl" refers to an unsaturated cyclic hydrocarbon radical with a conjugated $\pi$ electron system. Exemplary aryl groups include phenyl, naphthyl and the like. In some embodiments the aryl group is $(C_5-C_{20})$ aryl.

"Arylalkyl" refers to a straight chain alkyl, alkenyl or alkynyl group wherein one of the hydrogen atoms bound to the terminal carbon is replaced with an aryl group. Exemplary arylalkyl groups include benzyl, naphthylmethyl, benzylidene and the like.

"Growth factor" refers to an extracellularly active polypeptide that stimulates a cell to grow or proliferate by interacting with a receptor on the cell.

"Heteroalkyl" refers to an alkyl moiety wherein one or more carbon atoms are replaced with another atom such as N, P, O, S etc. Exemplary heteroalkyl groups include pyrrolidine, morpholine, piperidine, piperazine, imidazolidine, pyrazolidine, tetrahydrofuran, $(C_1-C_{10})$ substituted amines, $(C_2-C_6)$ thioethers and the like.

"Heteroaryl" refers to an aryl moiety wherein one or more carbon atoms are replaced with another atom such as N, P, O, S etc. Exemplary heteroaryl groups include carbazole, furan, imidazole, indazole, indole, isoquinoline, purine, pyrazine, pyrazole, pyridazine, pyridine, pyrrole, thiazole, thiophene, triazole and the like.

"Injury" includes any acute or chronic damage of an animal that results in degeneration or death of cells in the nervous system. Such cells include neuronal cells and non-neuronal cells. Injury includes stroke, non-hemorrhagic stroke, traumatic brain injury, perinatal asphyxia associated with fetal distress such as following abruption, cord occlusion or associated with intrauterine growth retardation, perinatal asphyxia associated with failure of adequate resuscitation or respiration, severe CNS insults associated with near miss drowning, near miss cot death, carbon monoxide inhalation, ammonia or other gaseous intoxication, cardiac arrest, coma, meningitis, hypoglycemia and status epilepticus, episodes of cerebral asphyxia associated with coronary bypass surgery, hypotensive episodes and hypertensive crises, and cerebral trauma. It is to be understood that the above examples are by way of illustration only, and are not intended to be a complete listing of injuries capable of being treated by the compounds and methods of this invention.

A "pharmaceutically acceptable excipient" refers to an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

A "pharmaceutically acceptable salt" refers to a salt that is pharmaceutically acceptable and has the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminium. Suitable organic salts include those formed with organic bases such as the amine bases e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid mono-salt or a di-acid salt; and similarly where there are more than two acidic groups present, some or all of such groups can be present as salts.

A "protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete.

"Substituted" refers to where one or more of the hydrogen atoms on an alkyl, heteroalkyl, alkenyl, alkynyl, aryl, heteroaryl or arylalkyl radical are independently replaced with another substitutent. Substituents include —R', —OR', —SR', —NR'R', —NO$_2$, —CN, —C(O)R', —C(O)OR', —C(O)NR'R', —C(NR')NR'R', —NR'—C(NR')—OR', —NR'—C(NR')—SR', NR'—C(NR)—NR'R', trihalomethyl and halogen where each R' is independently —H, alkyl, heteroalkyl, alkenyl, alkynyl, aryl, arylalkyl, heteroaryl or heteroarylalkyl.

A "therapeutically effective amount" means the amount that, when administered to an animal for treating a disease, is sufficient to effect treatment for a disease or an injury. A "therapeutically effective amount" means an amount that decreases adverse symptoms or findings, promotes desirable symptoms or findings, and/or treats an underlying disorder, and/or is curative.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

Implicit hydrogen atoms (such as the hydrogens on the pyrrole ring, etc.) are omitted from the formulae for clarity, but should be understood to be present.

Compounds of the Invention

Certain embodiments of this invention include novel derivatives of cPG having structures as described below for Formulas 1-7.

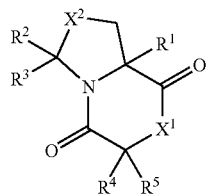

Formula 1

In certain embodiments, compounds of Formula 1 include substitutents where:

$X^1$ is selected from the group consisting of NR', O and S;

$X^2$ is selected from the group consisting of CH$_2$, NR', O and S;

$R^1$, $R^2$, $R^3$, $R^4$ and $R^5$ are independently selected from the group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted allynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^4$ and $R^5$ taken together are —CH$_2$—(CH$_2$)$_n$—CH$_2$— where n is an integer from 0-6;

or $R^2$ and $R^3$ taken together are —CH$_2$—(CH$_2$)$_n$—CH$_2$— where n is an integer from 0-6;

with the proviso that when $R^1$=methyl and $R^2$=$R^3$=$R^4$=H then $R^5 \neq$ benzyl and;

when $R^1$=H, at least one of $R^2$ and $R^3 \neq$ H.

In further embodiments, compounds of Formula 1 include substitutents where:

$R^1$=methyl, $R^2$=$R^3$=$R^4$=$R^5$=H, $X^1$=NH, $X^2$=CH$_2$;
$R^1$=allyl, $R^2$=$R^3$=$R^4$=$R^5$=H, $X^1$=NH, $X^2$=CH$_2$;
$R^1$=$R^2$=$R^3$=H, $R^4$=$R^5$=methyl, $X^1$=NH, $X^2$=CH$_2$;
$R^1$=$R^4$=$R^5$=H, $R^2$=$R^3$=methyl, $X^1$=NH, $X^2$=CH$_2$.

In other embodiments of the invention, compounds of Formula 1 include substitutents where;

$R^4$ and $R^5$ taken together are —CH$_2$—(CH$_2$)$_n$—CH$_2$— and:
$R^1$=methyl, $R^2$=$R^3$=H, n=0, $X^1$=NH, $X^2$=CH$_2$;
$R^1$=methyl, $R^2$=$R^3$=H, n=2, $X^1$=NH, $X^2$=CH$_2$;
$R^1$=allyl, $R^2$=$R^3$=H, n=0, $X^1$=NH, $X^2$=CH$_2$;
$R^1$=allyl, $R^2$=$R^3$=H, n=2, $X^1$=NH, $X^2$=CH$_2$.
$R^1$=methyl, $R^2$=$R^3$=H, n=3, $X^1$=NH, $X^2$=CH$_2$;
$R^1$=allyl, $R^2$=$R^3$=H, n=3, $X^1$=NH, $X^2$=CH$_2$.

In still other embodiments of the invention, compounds of Formula 1 include substitutents where $R^1$=methyl or allyl, $R^2$=$R^3$=$R^4$=H and $R^5$ is selected from the group consisting of the side chains of the amino acids: alanine, arginine, asparagine, aspartic acid, cysteine, glutamic acid, glutamine, histidine, isoleucine, leucine, lysine, methionine, proline, serine, threonine, tryptophan, tyrosine, valine, norvaline, norleucine, citruline, ornithine, homocysteine, homoserine, alloisoleucine, isovaline, sarcosine and the like.

In yet further embodiments of the invention, compounds of Formula 1 include substitutents where:

$R^1$=methyl, $R^2$=$R^3$=methyl, $R^4$=$R^5$=H, $X^1$=NH and $X^2$=S;
$R^1$=allyl, $R^2$=$R^3$=methyl, $R^4$=$R^5$=H, $X^1$=NH and $X^2$=S.

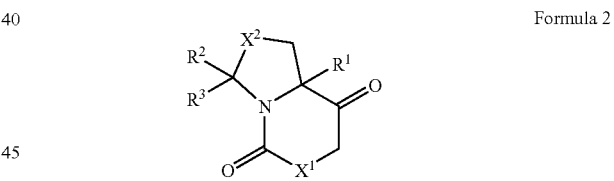

Formula 2

In other embodiments, compounds of Formula 2 include substitutents where:

$X^1$ is selected from the group consisting of NR', O and S;

$X^2$ is selected from the group consisting of CH$_2$, NR', O and S;

$R^1$, $R^2$ and $R^3$ are independently selected from the group consisting of group consisting of —H, —OR', —SR', —NR'R', —NO$_2$, —CN, —C(O)R', —C(O)OR', —C(O)NR'R', —C(NR')NR'R', trihalomethyl, halogen, alkyl, substituted alkyl, alkenyl, substituted alkenyl, heteroalkyl, substituted heteroalkyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^2$ and $R^3$ taken together are —CH$_2$—(CH$_2$)$_n$—CH$_2$— where n is an integer from 0-6;

with the proviso that at least one $R \neq$ H.

In still other embodiments, compounds of Formula 2 include substitutents where:
$R^1$=methyl, $R^2$=$R^3$=H, $X^1$=NH, $X^2$=$CH_2$;
$R^1$=allyl, $R^2$=$R^3$=H, $X^1$=NH, $X^2$=$CH_2$;
$R^1$=ethyl, $R^2$=$R^3$=H, $X^1$=NH, $X^2$=$CH_2$;
$R^1$=H, $R^2$=$R^3$=methyl, $X^1$=NH, $X^2$=$CH_2$.

In another series of embodiments, compounds of Formula 2 include substitutents where:
$R^1$=methyl, $R^2$=$R^3$=methyl, $X^1$=NH and $X^2$=S;
$R^1$=allyl, $R^2$=$R^3$=methyl, $X^1$=NH and $X^2$=S.

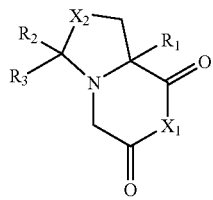

Formula 3

In other embodiments, compounds of Formula 3 include substitutents where:
$X^1$ is selected from the group consisting of NR', O and S;
$X^2$ is selected from the group consisting of $CH_2$, NR', O and S;
$R^1$, $R^2$ and $R^3$ are independently selected from the group consisting of group consisting of —H, —OR', —SR', —NR'R', —$NO_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;
or $R^2$ and $R^3$ taken together are —$CH_2$—($CH_2$),—$CH_2$— where n is an integer from 0-6.

In still other embodiments, compounds of Formula 3 include substitutents where:
$R^1$=methyl, $R^2$=$R^3$=H, $X^1$=NH, $X^2$=$CH_2$;
$R^1$=allyl, $R^2$=$R^3$=H, $X^1$=NH, $X^2$=$CH_2$;
$R^1$=ethyl, $R^2$=$R^3$=H, $X^1$=NH, $X^2$=$CH_2$;
$R^1$=H, $R^2$=$R^3$=methyl, $X^1$=NH, $X^2$=$CH_2$.

In further embodiments, compounds of Formula 3 include substitutents where:
$R^1$=methyl, $R^2$=$R^3$=methyl, $X^1$=NH and $X^2$=S;
$R^1$=allyl, $R^2$=$R^3$-methyl, $X^1$—NH and $X^2$=S.

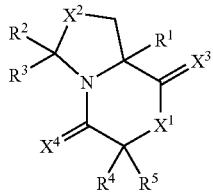

Formula 4

In further embodiments, compounds of Formula 4 include substitutents where:
$X^1$, $X^3$, and $X^4$ are independently selected from the group consisting of S, O, and NH;
$X^2$ is selected from the group consisting of S, O, $CH_2$ and NH;

$R^1$, $R^2$, $R^3$, $R^4$ and $R^5$ are independently selected from the group consisting of —H, —OR', —SR', —NR'R', —$NO_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;
or $R^4$ and $R^5$ taken together are —$CH_2$—($CH_2$)$_n$—$CH_2$— where n is an integer from 0-6;
or $R^2$ and $R^3$ taken together are —$CH_2$—($CH_2$),—$CH_2$— where n is an integer from 0-6;
with the proviso that at least one R≠H and that both $X^3$ and $X^4$≠O.

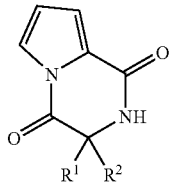

Formula 5

In still further embodiments, compounds of Formula 5 include substitutents where $R^1$ and $R^2$ are independently selected from the group consisting of group consisting of —H, —OR', —SR', —NR'R', —$NO_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;
or $R^1$ and $R^2$ taken together are —$CH_2$—($CH_2$),—$CH_2$— where n is an integer from 0-6.

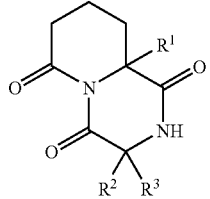

Formula 6

In other aspects, compounds of Formula 6 include substitutents where $R^1$, $R^2$ and $R^3$ are independently selected from the group consisting of group consisting of —H, —OR', —SR', —NR'R', —$NO_2$, —CN, —C(O)R', —C(O)OR', —C(O)NR'R', —C(NR')NR'R', trihalomethyl, halogen, alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl; each R' is independently selected from the group consisting of —H, alkyl, heteroalkyl, alkenyl, alkynyl, aryl, arylalkyl, heteroaryl and heteroarylalkyl;

or $R^2$ and $R^3$ taken together are —$CH_2$—$(CH_2)_n$—$CH_2$— where n is an integer from 0-6.

In yet other embodiments, compounds of Formula 6 include substitutents where $R^1$ is methyl or allyl.

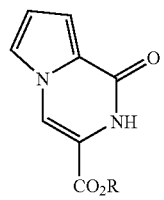

Formula 7

In yet further embodiments, compounds of Formula 7 include substitutents where R is selected from the group consisting of alkyl, substituted alkyl, heteroalkyl, substituted heteroalkyl, alkenyl, substituted alkenyl, alkynyl, substituted alkynyl, aryl, substituted aryl, heteroaryl, substituted heteroaryl, arylalkyl, substituted arylalkyl, heteroarylalkyl and substituted heteroarylalkyl.

Those with skill in the art will appreciate that the above structural representations can contain chiral centres, the number of which will depend on the different substitutents. The chirality may be either R or S at each centre. The structural drawings can represent only one of the possible tautomeric, conformational isomeric or enantiomeric forms, and it should be understood that the invention encompasses any tautomeric, conformational isomeric or enantiomeric form which exhibit biological or pharmacological activity as described herein.

Pharmacology and Utility

Certain aspects of this invention include the use of compounds of the invention in treatment or prevention of cell damage, degeneration and/or death in mammals in response to injury or disease. Some embodiments comprise delivering a composition containing a compound of the invention to an animal suffering from neural degeneration, and in some cases, conditions involving apoptotic and necrotic cell death. In some embodiments, compositions are desirable to treat an injury or disease of the CNS affecting or liable to affect brain cells. Compositions are provided that can also include one or more other agents that promote neural regeneration, decrease cell degeneration or death, or are neuroprotective.

Such other agents may be selected from the group consisting of for example, growth factors and associated derivatives, e.g., insulin-like growth factor-I [IGF-I], insulin-like growth factor-II [IGF-II], the tripeptide GPE, transforming growth factor-β1, activin, growth hormone, nerve growth factor, growth hormone binding protein, and/or IGF-binding proteins.

Other aspects of the invention include compositions and methods of promoting fasiculation of axons. By promoting formation of nerve bundles, compounds of the invention may be useful in treating conditions in which nerve processes (axons and/or dendrites) have become severed, such as in sharp force injuries, local areas of necrosis or disease, or other localized injuries to nerve processes.

In yet other embodiments, compositions and methods to treat or prevent cell damage and death in response to injury and disease, including CNS injury and disease, comprise administration of a therapeutic amount of a compound of the invention alone or in combination with other agents, after the insult. These embodiments can be particularly desirable in situations of unexpected injury, such as in cardiac arrest, trauma such as head injuries caused by automobile accidents, head wounds and the like.

In still further embodiments, compounds of the invention can be used either alone or in combination with other agents to prevent adverse effects of planned brain injury. Such conditions include CABG or other planned surgeries such as brain surgery, vascular surgery or other interventions that may lead to decreased perfusion of the nervous system. By treating an animal, such as a human being, in advance and/or simultaneously and/or after the surgery, adverse neurological effects can be ameliorated.

As indicated above, the present invention is broadly based upon the applicant's finding that compounds of the invention can protect cells, particularly nerve cells, against damage, loss of neurites, and/or apoptotic or necrotic cell death.

It is herein demonstrated that compounds of the invention exhibit neuroprotection in both cell culture and in animal models of neurodegenerative disease and can therefore be an effective addition or alternative to conventional therapies for neural degeneration.

Although the mechanism of the protective effects is not known, one possible mechanism involves protecting cells from apoptotic and necrotic cell death. However, regardless of the mechanism of action, compounds of the invention can be used as an effective therapy for a variety of neurological diseases, including hypoxia, ischemia and neurotoxin-induced nerve damage. Moreover, compounds of the invention can be used in the absence of any particular neurological deficit to promote neurite outgrowth and fasiculation of nerves. Thus, in situations in which cell death is not necessarily associated with the neurological disorder (e.g., axonal damage such as caused by spinal cord injury), administration of compounds of the invention may be an effective way of promoting neurite regeneration.

Therapeutic Applications

Compositions and methods of the invention find use in the treatment of animals, such as human patients, suffering from neural injury or disease. Still more generally, the compositions and methods of the invention find use in the treatment of mammals, such as human patients, suffering from nerve damage or potential apoptotic and/or necrotic cell death, due to injuries and diseases.

Specific conditions and diseases characterised by neuronal degeneration, apoptosis and/or necrosis include but are not limited to Alzheimer's disease, Parkinson's disease, multiple sclerosis, amyotrophic lateral sclerosis, spinal muscular atrophy, peripheral neuropathy, Creutzfeldt-Jakob disease, AIDS dementia, progressive supranuclear palsy, myelinopathia centralis diffusa (vanishing white matter disease), chronic neurodegenerative disease, Huntington's disease, stroke, ischemic injury, hypoxic injury, reperfusion injury, head injury, CNS trauma, epilepsy, cerebral ischemia, glaucoma, retinal disorders, optic neuropathy, optic neuritis, Down's syndrome, encephalomyelitis, meningitis, panencephalitis, neuroblastoma, schizophrenia and depression. Each of the above conditions exhibits pathophysiological findings and symptoms that are mimiced by neurotoxicity associated with glutamate toxicity.

Still more generally, the invention has application in the induction of nerve bundle formation following insult in the form of trauma, toxin exposure, asphyxia or hypoxia-ischemia. Additionally, the invention has application in the treatment or prevention of apoptosis in response to injury or disease in the form of cancers, viral infections, autoimmune diseases, neurological diseases and injuries and cardiovascular diseases.

Treatment may be given before an injury, for example, before elective surgery. Examples of relevant elective procedures include neural surgery, in which retraction of lobes of the brain may lead to cerebral oedema, or heart operations, such as valve replacement, in which inevitable small emboli are said to lead to detectable impairment of brain function in some 75% of cases.

Determining Efficacy

The anti-apoptotic and anti-necrotic activity of compounds of the invention on cellular death can be measured in vivo using cell counts by methods known to those skilled in the art including the methods of Klempt et al. (Klempt et al., 1992, *Molecular Brain Research:* 13: 93-101), microscopic examinations of morphology, cell counts of surviving and dead neurons stained with thionin/fachsin and the like. Compounds of the invention can also be measured in vitro using mass spectroscopy, immunological, or chromatographic methods known in the art.

CNS damage may for example be measured clinically by the degree of permanent neurological deficit cognitive function, and/or propensity to seizure disorders. Herein are disclosed histological techniques suitable for measuring effects in vivo.

The therapeutic ratio of a compound is understood to be the ratio of (1) the mean dose that causes adverse side effect over (2) the mean dose that causes a desirable therapeutic effect. Thus, for compounds for which have therapeutic effects at relatively low doses and undesirable side effects at high doses, the therapeutic ratio is >1. Therapeutic ratio can be determined, for example, by comparing the dose that produces significant weight loss (or other observable side-effect) divided by the dose that produces anti-apoptotic and anti-necrotic activity in a suitable in vivo animal species such as the rat or mouse. Suitable animal systems useful for determining therapeutic effects of compounds of this invention include hypoxic-ischemic injury (Sirimanne et al., 1994 *Journal of Neuroscience Methods:* 55: 7-14), experimental immune encephalomyelitis (Mendel et al., 1995 *Eur. J. Immunol.:* 25: 1951-1959) and glutamate toxicity.

Pharmaceutical Compositions and Administration

Compounds of the invention can be administered as part of a medicament or pharmaceutical preparation. This can involve combining a compound of the invention with any pharmaceutically appropriate carrier, adjuvant or excipient. The selection of the carrier, adjuvant or excipient will of course usually be dependent upon the route of administration to be employed.

In general, compounds of this invention will be administered in therapeutically effective amounts by any of the usual modes known in the art, either singly or in combination with other conventional therapeutic agents for the disease being treated. A therapeutically effective amount may vary widely depending on the disease or injury, its severity, the age and relative health of the animal being treated, the potency of the compound(s), and other factors. As anti-apoptotic and anti-necrotic agents, therapeutically effective amounts of compounds of this invention may range from 0.001 to 100 milligrams per kilogram mass of the animal, with lower doses such as 0.001 to 0.1 mg/kg being appropriate for administration through the cerebrospinal fluid, such as by intracerebroventricular administration, and higher doses such as 1 to 100 mg/kg being appropriate for administration by methods such as oral, systemic (e.g. transdermal), or parenteral (e.g. intravenous) administration. A person of ordinary skill in the art will be able without undue experimentation, having regard to that skill and this disclosure, to determine a therapeutically effective amount of a compound of this invention for a given disease or injury.

Compounds of the invention may be administered peripherally via any peripheral route known in the art. These can include parenteral routes for example injection into the peripheral circulation, subcutaneous, intraorbital, ophthalmic, intraspinal, intracisternal, topical, infusion (using e.g. slow release devices or minipumps such as osmotic pumps or skin patches), implant, aerosol, inhalation, scarification, intraperitoneal, intracapsular, intramuscular, intranasal, oral, buccal, transdermal, pulmonary, rectal or vaginal. The compositions can be formulated for parenteral administration to humans or other mammals in therapeutically effective amounts (e.g. amounts which eliminate or reduce the patient's pathological condition) to provide therapy for the neurological diseases described above.

Desirably, if possible, when administered as anti-apoptotic and anti-necrotic agents, compounds of this invention will be administered orally. The amount of a compound of this invention in the composition may vary widely depending on the type of composition, size of a unit dosage, kind of excipients, and other factors well known to those of ordinary skill in the art. In general, the final composition may comprise from 0.0001 percent by weight (% w) to 10% w of the compound of this invention, preferably 0.001% w to 1% w, with the remainder being the excipient or excipients.

Other convenient administration routes include subcutaneous injection (e.g. dissolved in a physiologically compatible carrier such as 0.9% sodium chloride) or direct administration to the CNS. Using stereotactic devices and accurate maps of an animals' CNS, a compound may be injected directly into a site of neural damage. Such routes of administration may be especially desired in situations in which perfusion of that location is compromised either by decreased vascular perfusion or by decreased cerebral spinal fluid (CSF) flow to that area. Examples include administration by lateral cerebroventricular injection or through a surgically inserted shunt into the lateral cerebroventricle of the brain of the patient, intraveneously, direct injection into the desired location or other routes.

The effective amount of compound in the CNS may be increased by administration of a pro-drug form of a compound which comprises a compound of the invention and a carrier, where the carrier is joined to a compound of the invention by a linkage which is susceptible to cleavage or digestion within the patient. Any suitable linkage can be employed which will be cleaved or digested following administration.

However, there is no intention on the part of the applicants to exclude other forms of administration.

In further embodiments of the invention, restoring nerve function in an animal can comprise administering a therapeutic amount of a compound of the invention in combination with another neuroprotective agent, selected from, for example, growth factors and associated derivatives (insulin-like growth factor-I [IGF-I], insulin-like growth factor-II [IGF-II], transforming growth factor-#1, activin, growth hormone, nerve growth factor, growth hormone binding protein, IGF-binding proteins [especially IGFBP-3], basic fibroblast growth factor, acidic fibroblast growth factor, the hst/Kfgk gene product, FGF-3, FGF-4, FGF-6, keratinocyte growth factor, androgen-induced growth factor. Additional members of the FGF family include, for example, int-2, fibroblast growth factor homologous factor-1 (FHF-1), FHF-2, FHF-3 and FHF-4, karatinocyte growth factor 2, glial-activating factor, FGF-10 and FGF-16, ciliary neurotrophic factor, brain derived growth factor, neurotrophin 3, neurotrophin 4, bone morphogenetic protein 2 [BMP-2], glial-cell line derived neurotrophic factor, activity-dependant neurotrophic factor, cytokine leukaemia inhibiting factor, oncostatin M, interleukin), $\alpha$-, $\beta$-, $\gamma$-, or consensus interferon, and TNF-$\alpha$. Other forms of neuroprotective therapeutic agents include, for example, clomethiazole; kynurenic acid, Semax, tacrolimus, L-threo-1-phenyl-2-decanoylamino-3-morpholino-1-propanol, andrenocorticotropin-(4-9) analogue [ORG 2766] and dizolcipine [MK-801], selegiline; glutamate antagonists such as, NPS1506, GV1505260, MK-801, GV150526; AMPA antagonists such as 2,3-dihydroxy-6-nitro-7-sulfamoylbenzo (f)quinoxaline (NBQX), LY303070 and LY300164; anti-inflammatory agents directed against the addressin MAd-CAM-1 and/or its integrin $\alpha$4 receptors ($\alpha$4$\beta$1 and $\alpha$4$\beta$7), such as anti-MAdCAM-1mAb MECA-367 (ATCC accession no. HB-9478).

A compound is suitably administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773, 919; EP 58,481), copolymers of L-glutamic acid and gamma-ethyl-L-glutamate (Sidman et al., 1983, *Biopolymers:* 22: 547-56), poly(2-hydroxyethyl methacrylate) (Langer et al., 1981, *J. Biomed. Mater. Res.:* 15: 267), ethylene vinyl acetate (Langer et al., 1981, *J. Biomed. Mater. Res.:* 15: 267), or poly-D-(−)-3-hydroxybutyric acid (EP 133,988). Sustained-release compositions also include a liposomally entrapped compound. Liposomes containing the compound are prepared by methods known per se: DE 3,218,121, EP 52,322, EP 36,676, EP 88,046, EP 143,949, EP 142,641, Japanese Pat. Appln. 83-118008, U.S. Pat. Nos. 4,485,045 and 4,544, 545, and EP 102,324. Ordinarily, the liposomes are of the small (from or about 200 to 800 Angstroms) unilamellar type in which the lipid content is greater than about 30 mol percent cholesterol, the selected proportion being adjusted for the most efficacious therapy.

For parenteral administration, in one embodiment the compound is formulated generally by mixing each at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation.

Generally, the formulations are prepared by contacting the compound uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

A carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc.

A compound is typically formulated in such vehicles at a pH of from or about 4.5 to 8. It will be understood that use of certain of the foregoing excipients, carriers, or stabilizers will result in the formation of salts of the compound. The final preparation may be a stable liquid or lyophilized solid.

Formulations of the compound in pharmaceutical compositions can also include adjuvants. Typical adjuvants which may be incorporated into tablets, capsules, and the like are a binder such as acacia, corn starch, or gelatin; an excipient such as microcrystalline cellulose; a disintegrating agent like corn starch or alginic acid; a lubricant such as magnesium stearate; a sweetening agent such as sucrose or lactose; a flavouring agent such as peppermint, wintergreen, or cherry. When the dosage form is a capsule, in addition to the above materials, it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a colouring agent, and a flavouring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants, and the like can be incorporated according to accepted pharmaceutical practice.

For injection, intraventricular administration, and other invasive routes of administration, the compounds used must be sterile. Sterility may be accomplished by any method known in the art, for example filtration through sterile filtration membranes (e.g., 0.2 micron membranes). Therapeutic compositions generally are placed into a container having a sterile access port, for example, an intravenous solution bag or vial having a stopper able to be pierced by a hypodermic injection needle.

A pharmaceutical formulation ordinarily will be stored in unit or multi-dose containers, for example, in sealed ampoules or vials, as an aqueous solution or as a lyophilized formulation for reconstitution. As an example of a lyophilized formulation, 10 mL vials are filled with 5 mL of sterile-filtered 1% (w/v) aqueous solution of compound, and the resulting mixture is lyophilized. The infusion solution is prepared by reconstituting the lyophilized compound using bacteriostatic Water-for-Injection. It can be readily appreciated that other dosage forms and types of preparations can be used, and all are considered to be part of this invention.

Preparation of the Compounds

Starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to the person of ordinary skill in the art following procedures described in such references as Fieser and Fieser's Reagents for Organic Synthesis, vols 1-17, John Wiley and Sons, New York, N.Y., 1991; Rodd's Chemistry of Carbon Compounds, vols. 1-5 and supplements, Elsevier Science Publishers, 1989; Organic Reactions, vols. 1-40, John Wiley and Sons, New York, N.Y., 1991; March J; Advanced Organic Chemistry, $4^{th}$ ed. John Wiley and Sons, New York, N.Y., 1992; and Larock: Comprehensive Organic Transformations, VCH Publishers, 1989. In most instances, amino acids and their esters or amides, and protected amino acids, are widely commercially available; and the preparation of modified amino acids and their amides or esters are extensively described in the chemical and biochemical literature and thus well-known to persons of ordinary skill in the art.

Starting materials, intermediates, and compounds of this invention may be isolated and purified using conventional techniques, including filtration, distillation, crystallization, chromatography, and the like. They may be characterized using conventional methods, including physical constants and spectral data.

Compounds of this invention may be prepared by the methods described below and as given in the Examples.

Compounds of this invention are generally cyclic dipeptides (bicyclic 2,5-diketopiperazines) or analogues thereof. In general, they may be prepared by methods such as are already well-known to persons of ordinary skill in the art of peptide and modified peptide synthesis, following the reaction schemes set forth in the Figures following this specification, or by following other methods well-known to those of ordinary skill in the art of the synthesis of peptides and analogues. See for example, Bodanzsky: Principles of Peptide Synthesis, Berlin, N.Y.: Springer-Verlag 1993.

Synthesis of the diketopiperazine compounds of this invention may be by solution-phase synthesis as discussed in the Examples or via the solid-phase synthesis method exemplified by Merrifield et al. 1963 *J. Amer. Chem. Soc.*: 85, 2149-2156. Solid phase synthesis may be performed using commercial peptide synthesizers, such as the Applied Biosystems Model 430A, using the protocols established for the instrument.

Specific examples of diketopiperazine synthesis can be found in the Examples following and in, for example, Fischer, 2003, *J. Peptide Science:* 9: 9-35 and references therein. A person of ordinary skill in the art will have no difficulty, taking account of that skill and the knowledge available, and of this disclosure, in developing one or more suitable synthetic methods for compounds of this invention.

The choice of appropriate protecting groups for the method chosen (solid-phase or solution-phase), and of appropriate substrates if solid-phase synthesis is used, will be within the skill of a person of ordinary skill in the art. Appropriate protecting groups for peptide synthesis include t-butyloxycarbonyl (Boc), fluorenylmethyloxycarbonyl (Fmoc), Benzyl (Bzl), t-amyloxycarbonyl (Aoc), tosyl (Tos), benzyloxycarbonyl (Z or Cbz), o-bromo-benzyloxycarbonyl (BrZ) and the like. Additional protecting groups are identified in Merrifield, cited above, as well as in McOmie J F W: Protective Groups in Organic Chemistry, Plenum Press, New York, 1973.

The choice of coupling agent for the method chosen will also be within the skill of a person of ordinary skill in the art. Suitable coupling agents include DCC(N, N'-Dicyclohexylcarbodiimide), Bop (Benzotriazole-1-yl-oxy-tris-(dimethylamino)-phosphonium hexafluorophosphate), PyBop (Benzotriazol-1-yl-oxytripyrrolidinophosphonium hexafluorophosphate), BopCl (bis(2-oxo-3-oxazolidinyl) phosphinic chloride), 2-Chloro-1,3-dimethylimidazolidinium hexafluorophosphate (CIP) and the like.

For example, compounds may be synthesized by the following methods.

Scheme 1:

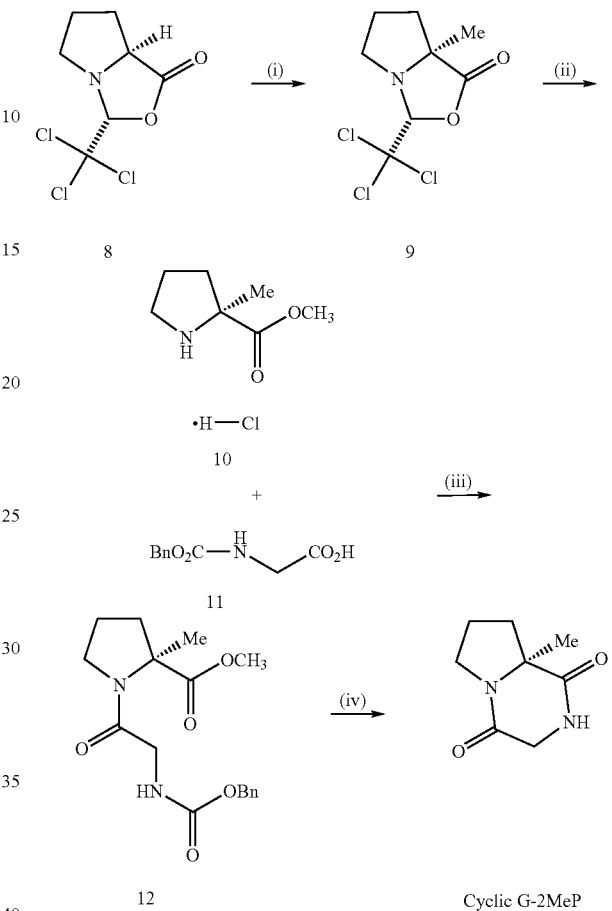

Reagents, conditions and yields: (i) LDA, THF, -78° C., iodomethane, -78->-50° C., 2 h (63%); (ii) SOCl$_2$, CH$_3$OH, reflux, N$_2$, 2.5 h (98%); (iii) Et$_3$N, BoPCl, CH$_2$Cl$_2$, RT, N$_2$, 20.5 h (78%); (iv) 10% Pd/C, CH$_3$OH, RT, 15 h (98%).

Oxazolidinone 8 can be synthesized by reaction of chloral with proline. This oxazolidinone can then reduced using lithium diisopropylamide (LDA), followed by addition of a methyl group using iodomethane to produce oxazolidinone 9. Thionyl chloride or acetyl chloride can be used to produce the methyl ester of 2-methyl proline as in Scheme 1 above. It will be apparent to those skilled in the art that the iodomethane can be replaced with a suitable halogen compound to produce various analogues modified at the carbon 2 position. For example, use of iodoethane will produce 2-ethyl proline; use of allylbromide will produce 2-allyl proline and use of benzylbromide will produce 2-benzyl proline.

The proline protected at the C-terminus can then be coupled to an amino acid protected at the N-terminal with a suitable protecting group such as Cbz, Boc or Fmoc. Suitable coupling reagents for this procedure will be apparent to those skilled in the art and include such reagents as bis(2-oxo-3-oxazolidinyl)phosphinic chloride (BoPCl), dicyclohexylcarbodiimide (DCC), 2-Chloro-1,3-dimethylimidazolidinium hexafluorophosphate (CIP) (Babu and Ananda, 2001, *Indian J. Chem. Sect. B.:* 40B(1): 70; Akaji and Aimoto 2001, *Tetrahedron,* 57(9), 1749). The dipeptide thus formed can then be selectively de-protected at the N-terminus, using for example, hydrogenation to remove Cbz groups and trifluoroacetic acid (TFA) to remove Boc groups. The molecule then cyclises with elimination of the methoxy group of the methyl ester to give the diketopiperazine.

The amino acid used in scheme 1 is glycine which gives compounds of formula 1 where $R^4=R^5=H$. Replacement of glycine with other amino acids will result in compounds of formula 1 where $R^4=H$ and $R^5$ is equivalent to the side chain of the respective amino acid.

Scheme 2:

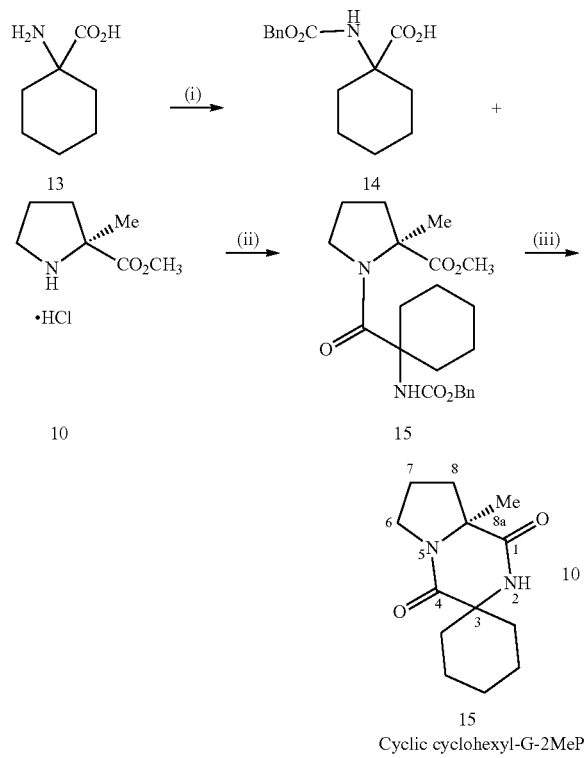

Cyclic cyclohexyl-G-2MeP

Reagents, conditions, and yields: (i) BnO$_2$CCl, Na$_2$CO$_3$, H$_2$O-dioxane (3:1), 19 h, 96%; (ii) Et$_3$N, HOAt, CIP, 1,2-dichloroethane, reflux, N$_2$, 19 h (23%); (iii) 10% Pd/C, CH$_3$OH, RT, 17 h (65%).

1-Aminocyclohexanecarboxylic acid 13 (Fluka) can be protected at the N-terminus using a protecting group such as Cbz. This compound can then be coupled to a proline derivative suitably protected at the C-terminus using a suitable coupling agent such as 2-Chloro-1,3-dimethylimidazolidinium hexafluorophosphate (CIP) as in Scheme 2. The dipeptide thus formed can then be selectively de-protected at the N-terminus via hydrogenation for example, and the resultant elimination of the methoxy group of the methyl ester produces the diketopiperazine. It will be apparent to those skilled in the art that replacement of the 1-aminocyclohexanecarboxylic acid with analogous compounds such as 1-aminocyclopentanecarboxylic acid or 1-aminocyclopropanecarboxylic acid will be possible. It will also be apparent that the methyl group at the C-2 (carbon centre 8a in scheme 2) position of proline may be replaced with other substitutents such as ethyl, allyl and benzyl as discussed above.

All patent and literature references cited throughout the specification are expressly incorporated by reference in their entirety.

EXAMPLES

The present invention is further illustrated by the following examples. These examples are offered by way of illustration only and are not intended to limit the scope of the invention.

General Methods

Flash chromatography was performed using Scharlau 60 (40-60 μm mesh) silica gel. Analytical thin layer chromatography was carried out on 0.20 mm pre-coated silica gel plates (ALUGRAM® SIL G/UV$_{254}$) and compounds visualized using UV fluorescence, or heating of plates dipped in potassium permanganate in alkaline solution.

Melting points in degrees Celsius (° C.) were determined on an Electrothermal® melting point apparatus and are uncorrected.

Optical rotations were measured at 20° C. on a Perkin Elmer 341 polarimeter using 10 cm path length cells and are given in units of $10^{-1}$ degcm$^2$ g$^{-1}$. Samples were prepared in the solvent indicated at the concentration specified (measured in g/100 cm$^3$). IR spectra were recorded on a Perkin Elmer Spectrum One FT-IR spectrometer. The samples were prepared as thin films on sodium chloride discs or as solids in potassium bromide discs. A broad signal indicated by br. The frequencies (υ) as absorption maxima are given in wavenumbers (cm$^{-1}$).

NMR spectra were recorded on a Bruker AVANCE DRX400 ($^1$H, 400 MHz; $^{13}$C, 100 MH) or a Bruker AVANCE 300 ($^1$H, 300 MHz; $^{13}$C, 75 MHz) spectrometer at ambient temperatures. For $^1$H NMR data chemical shifts are described in parts per million downfield from SiMe$_4$ and are reported consecutively as position ($\delta_H$), relative integral, multiplicity (s=singlet, d=doublet, t=triplet, dd=doublet of doublets, m=multiplet, br=broad), coupling constant (J/Hz) and assignment. For $^{13}$C NMR data, chemical shifts are described in parts per million relative to CDCl$_3$ and are reported consecutively as position ($\delta_C$), degree of hybridization as determined by DEPT experiments, and assignment. $^1$H NMR spectra were referenced internally using SiMe$_4$ ($\delta$0.00) or CDCl$_3$ ($\delta$7.26). $^{13}$C NMR spectra were referenced internally using CDCl$_3$ ($\delta$77.0). When two sets of peaks arise in the NMR spectra due to different conformations around the glycine-proline amide bond, the chemical shift for the minor cis conformer is marked with an asterisk (*).

Accurate mass measurements were recorded on a VG-70SE mass spectrometer.

Hexane and dichloromethane were distilled prior to use. Methanol was dried using magnesium turnings and iodine, and distilled under nitrogen. Triethylamine was dried over calcium hydride and distilled under nitrogen.

Example 1

Synthesis of (8aS)-Methyl-hexahydropyrrolo[1,2-a]pyrazine-1,4-dione (Cyclic G-2MeP)

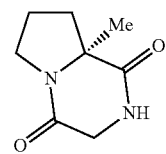

21

Scheme 1:

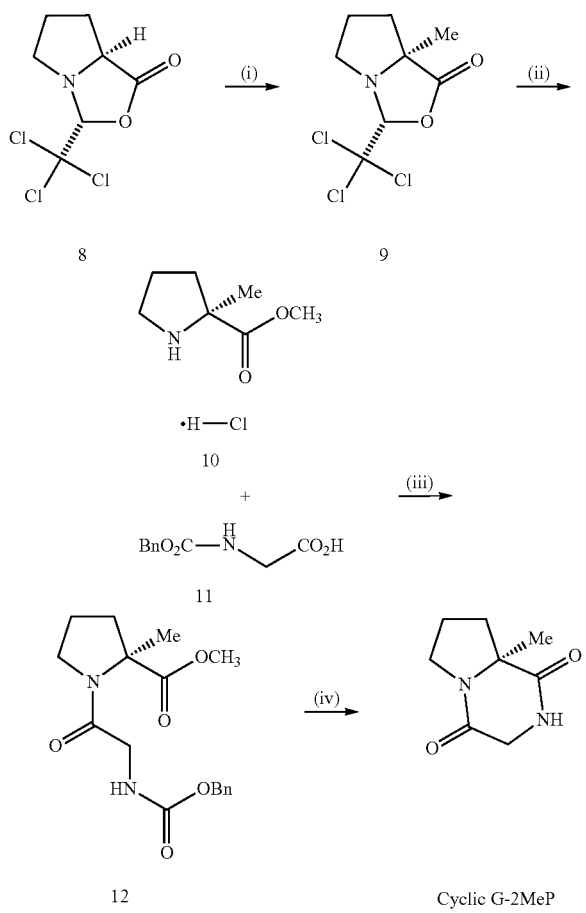

Reagents, conditions and yields: (i) LDA, THF, -78° C., iodomethane, -78-> -50° C., 2 h (63%); (ii) SOCl$_2$, CH$_3$OH, reflux, N$_2$, 2.5 h (98%); (iii) Et$_3$N, BoPCl, CH$_2$Cl$_2$, RT, N$_2$, 20.5 h (78%); (iv) 10% Pd/C, CH$_3$OH, RT, 15 h (98%).

(2R,5S)-4-Methyl-2-trichloromethyl-1-aza-3-oxabicyclo[3.3.0]octan-4-one 9 n-BuLi (1.31 M, 4.68 cm$^3$, 6.14 mmol) was added dropwise to a stirred solution of diisopropylamine (0.86 cm$^3$, 6.14 mmol) in dry tetrahydrofuran (10 cm$^3$) at −78° C. under an atmosphere of nitrogen. The solution was stirred for 5 min, warmed to 0° C. and stirred for 15 min. The solution was then added dropwise to a solution of oxazolidinone 8 (1.00 g, 4.09 mmol) in dry tetrahydrofuran (20 cm$^3$) at −78° C. over 20 min (turned to a dark brown colour), stirred for a further 30 min then iodomethane (0.76 cm$^3$, 12.3 mmol) was added dropwise over 5 min. The solution was warmed to −50° C. over 2 h. Water (15 cm$^3$) was added and the solution warmed to room temperature and extracted with chloroform (3×40 cm$^3$). The combined organic extracts were dried (MgSO$_4$), filtered and evaporated to dryness in vacuo to give a dark brown semisolid. Purification of the residue by flash column chromatography (15% ethyl acetate-hexane) afforded oxazolidinone 9 (0.67 g, 63%) as a pale yellow solid: mp 55-57° C. (lit., 57-60° C.); $\delta_H$ (300 MHz, CDCl$_3$) 1.53 (3H, s, CH$_3$), 1.72-2.02 (3H, m, Proβ-H and Proγ-H$_2$), 2.18-2.26 (1H, m, Proβ-H), 3.15-3.22 (1H, m, Proδ-H), 3.35-3.44 (1H, m, Proδ-H) and 4.99 (1H, s, NCH).

Methyl L-2-methylprolinate hydrochloride 10 a) Using Acetyl Chloride

Oxazolidinone 9 (0.60 g, 2.33 mmol) was dissolved in dry methanol (15 cm$^3$) under an atmosphere of nitrogen and acetyl chloride (0.33 cm$^3$, 4.66 mmol) was added dropwise to the ice-cooled solution. The solution was heated under reflux for 4.5 h, then the solvent removed under reduced pressure to give a brown oil which was purified by flash column chromatography (10% CH$_3$OH—CH$_2$Cl$_2$) affording the hydrochloride 10 (0.2 g, 48%) as a flaky white solid: mp 107-109° C. (lit., 106-108° C.); $\delta_H$ (300 MHz, CDCl$_3$) 1.81 (3H, s, CH$_3$), 1.93-2.14 (3H, m, Proβ-H$_A$H$_B$ and Proγ-H$_2$), 2.33-2.39 (1H, m, Proβ-H$_A$H$_B$), 3.52-3.56 (2H, m, Proδ-H$_2$) and 3.82 (3H, s, CO$_2$CH$_3$).

B) Using Thionyl Chloride

An ice-cooled solution of oxazolidinone 9 (53 mg, 0.21 mmol) in dry methanol (1 cm$^3$) was treated dropwise with thionyl chloride (0.045 cm$^3$, 0.62 mmol). The solution was heated under reflux for 2.5 h, cooled and the solvent removed under reduced pressure to yield a brown oil. The oil was dissolved in toluene (5 cm$^3$), concentrated to dryness to remove residual thionyl chloride and methanol then purified by flash column chromatography (10% CH$_3$OH—CH$_2$Cl$_2$) to afford the hydrochloride 10 (16 mg, 43%) as a flaky white solid. The $^1$H NMR assignments were in agreement with those reported above.

Methyl-N-benzyloxycarbonyl-glycyl-L-2-methylprolinate 12

Dry triethylamine (0.27 cm$^3$, 1.96 mmol) was added dropwise to a solution of hydrochloride 10 (0.11 g, 0.61 mmol) and N-benzyloxycarbonyl-glycine 11 (98.5%) (0.17 g, 0.79 mmol) in dry dichloromethane (35 cm$^3$) under an atmosphere of nitrogen at room temperature, and the reaction mixture stirred for 10 min. Bis(2-oxo-3-oxazolidinyl)phosphinic chloride (BoPCl, 97%) (0.196 g, 0.77 mmol) was added and the resultant colourless solution was stirred for 20.5 h. The solution washed successively with 10% aqueous hydrochloric acid (30 cm$^3$) and saturated aqueous sodium hydrogen carbonate (30 cm$^3$), dried (MgSO$_4$), filtered and evaporated to dryness in vacuo. Purification of the resultant residue by flash column chromatography (50-80% ethyl acetate-hexane; gradient elution) yielded dipeptide 12 (0.18 g, 92%) as a colourless oil. Amide 12 was shown to exist as a 98:2 trans:cis mixture of conformers by $^{13}$C NMR analysis (the ratio was estimated from the relative intensities of the resonances at δ20.8 and 23.5 assigned to the Proγ-C atoms of the minor and major conformers, respectively): [α]$_D$−33.0 (c 1.0 in MeOH); $\nu_{max}$ (film)/cm$^{-1}$ 3406, 2952, 1732, 1651, 1521, 1434, 1373, 1329, 1310, 1284, 1257, 1220, 1195, 1172, 1135, 1107, 1082, 1052, 1029, 986, 965, 907, 876, 829, 775, 738 and 699; $\delta_H$ (300 MHz, CDCl$_3$) 1.49 (3H, s, CH$_3$), 1.77-2.11 (4H, m, Proβ-H$_2$ and Proγ-H$_2$), 3.43-3.48 (2H, m, Proδ-H$_2$), 3.61 (3H, s, OCH$_3$), 3.85-3.89 (2H, m, Glyα-H$_2$), 5.04 (2H, s, PhCH$_2$), 5.76 (1H, br s, N—H) and 7.21-7.28 (5H, s, ArH); $\delta_C$ (75 MHz, CDCl$_3$) 13.8* (CH$_3$, Proα-CH$_3$), 21.1 (CH$_3$, Proα-CH$_3$), 20.8* (CH$_2$, Proγ-C), 23.5 (CH$_2$, Proγ-C), 38.0 (CH$_2$, Proβ-C), 40.8* (CH$_2$, Proβ-C), 43.3 (CH$_2$, Glyα-C), 45.5* (CH$_2$, Glyα-C), 46.6 (CH$_2$, Proδ-C), 48.7* (CH$_2$, Proδ-C), 51.9* (CH$_3$, OCH$_3$), 52.1 (CH$_3$, OCH$_3$), 60.0* (quat., Proα-C), 66.0 (quat., Proα-C), 66.3 (CH$_2$, PhCH$_2$), 68.6* (CH$_2$, PhCH$_2$), 127.5 (CH, Ph), 127.6 (CH, Ph), 127.9* (CH, Ph), 128.1 (CH, Ph), 128.3* (CH, Ph), 136.2 (quat, Ph), 155.9 (quat., NCO$_2$), 166.0 (quat., Gly-CON), 169.4* (quat., Gly- CON) and 173.6 (quat., CO$_2$CH$_3$); m/z (EI+) 334.1535 (M$^+$. C$_{17}$H$_{22}$N$_2$O$_5$ requires 334.1529).

(8aS)-Methyl-hexahydropyrrolo[1,2-a]pyrazine-1,4-dione (Cyclic G-2MeP)

To a solution of dipeptide 12 (0.167 g, 0.51 mmol) in methanol (8.0 cm$^3$) was added 10% Pd on activated charcoal (8.1 mg, 0.076 mmol) and the vessel flushed with hydrogen gas. The resulting suspension was stirred vigorously under an atmosphere of hydrogen for 15 h. The mixture was then filtered through a Celite pad then a short plug of silica gel with methanol, and the solvent removed under reduced pressure to produce cyclic G-2MeP (83 mg, 98%) as a yellow solid: mp 133-135° C.; [α]$_D$–128.1 (c 0.52 in MeOH); δ$_H$ (300 MHz, CDCl$_3$) 1.36 (3H, s, CH$_3$), 1.87-2.01 (3H, m, Proβ-H$_A$H$_B$ and Proγ-H$_2$), 2.07-2.21 (1H, m, Proβ-H$_A$H$_B$), 3.45-3.64 (2H, m, Proδ-H$_2$), 3.82 (1H, dd, J 17.1 and 4.1, CH$_A$H$_B$NH), 3.99 (1H, d, J 17.1, CH$_A$H$_B$NH) and 7.66 (1H, br s, N—H); δ$_C$ (75 MHz, CDCl$_3$) 20.2 (CH$_2$, Proγ-C), 23.2 (CH$_3$, Proα-CH$_3$), 35.0 (CH$_2$, Proβ-C), 44.7 (CH$_2$, Proδ-C), 45.9 (CH$_2$, CH$_2$NH), 63.8 (quat., Proα-C), 163.3 (quat., NCO) and 173.3 (quat., CONH; m/z (EI+) 168.08986 (M$^+$. C$_8$H$_{12}$N$_2$O$_2$ requires 168.08988).

Example 2

Synthesis of (8aS)-Methyl-spiro[cyclohexane-1,3(4H)-tetrahydropyrrolo[1,2-a]pyrazine]-1,4(2H)-dione (Cyclic cyclohexyl-G-2MeP)

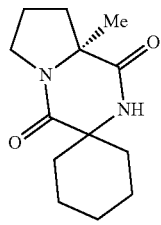

Scheme 2:

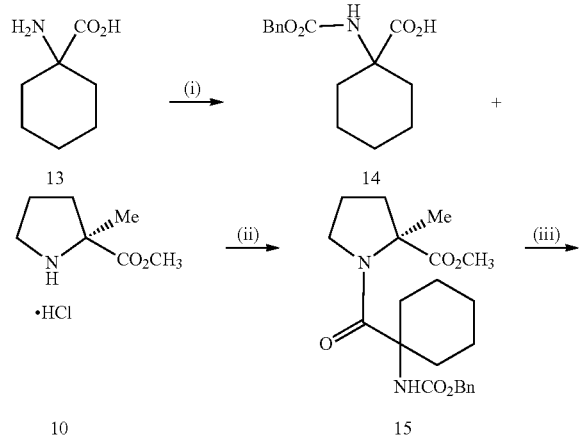

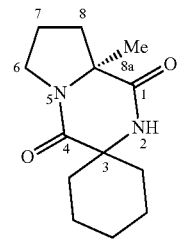

Cyclic cyclohexyl-G-2MeP

Reagents, conditions, and yields: (i) BnO$_2$CCl, Na$_2$CO$_3$, H$_2$O-dioxane (3:1), 19 h, 96%; (ii) Et$_3$N, HOAt, CIP, 1,2-dichloroethane, reflux, N$_2$, 19 h (23%); (iii) 10% Pd/C, CH$_3$OH, RT, 17 h (65%).

N-benzyloxycarbonyl-1-aminocyclohexane-1-carboxylic acid (14)

To a suspension of 1-aminocyclohexanecarboxylic acid 13 (0.72 g, 5.02 mmol) and sodium carbonate (1.6 g, 15.1 mmol) were dissolved in water-dioxane (21 cm$^3$, 3:1) was added benzyl chloroformate (0.79 cm$^3$, 5.52 mmol) was added dropwise and the solution was stirred at room temperature for 19.5 h. The aqueous layer was washed with diethyl ether (60 cm$^3$), acidified with 2 M HCl and extracted with ethyl acetate (2×60 cm$^3$). The organic layers were combined, dried (MgSO$_4$), filtered and evaporated under reduced pressure to produce a colourless oil, which solidified on standing to crude carbamate 14 (1.23 g, 88%) as a white solid: mp 152-154° C. (f, 148-150° C.); 9 (400 MHz, CDCl$_3$) 1.27-1.56 (3H, m, 3× cyclohexyl-H), 1.59-1.73 (3H, m, 3× cyclohexyl-H), 1.85-1.91 (2H, m, 2× cyclopentyl-H), 2.05-2.09 (2H, m, 2×cyclopentyl-H), 5.02 (1H, br s, N—H), 5.12 (2H, s, OCH$_2$Ph) and 7.27-7.36 (5H, s, Ph); δ$_C$ (100 MHz, CDCl$_3$) 21.1 (CH$_2$, 2× cyclohexyl-C), 25.1 (CH$_2$, 2× cyclohexyl-C), 32.3 (CH$_2$, cyclohexyl-C), 59.0 (quat., 1-C), 67.1 (CH$_2$, OCH$_2$Ph), 128.1 (CH, Ph), 128.2 (CH, Ph), 128.5 (CH, Ph), 136.1 (quat., Ph), 155.7 (quat., NCO$_2$) and 178.7 (quat., CO$_2$H).

Methyl-N-benzyloxycarbonyl-cyclohexyl-glycyl-L-2-methylprolinate (15)

Dry triethylamine (0.21 cm$^3$, 1.5 mmol) was added dropwise to a solution of hydrochloride 10 (84.0 mg, 0.47 mmol), carboxylic acid 14 (0.17 g, 0.61 mmol) and 1-hydroxy-7-azabenzotriazole (16 mg, 0.12 mmol) in dry 1,2-dichloroethane (26 cm$^3$) under an atmosphere of nitrogen at room temperature, and the reaction mixture stirred for 10 min. 2-Chloro-1,3-dimethylimidazolidinium hexafluorophosphate (0.13 g, 0.47 mmol) was added and the resultant solution heated under reflux for 21 h, then washed successively with 10% aqueous hydrochloric acid (30 cm$^3$) and saturated aqueous sodium hydrogen carbonate (30 cm$^3$), dried (MgSO$_4$), filtered and evaporated to dryness in vacuo. Purification of the resultant residue by flash column chromatography (40-50% ethyl acetate-hexane; gradient elution) yielded amide 15 (16 mg, 9%) as a white solid. Amide 15 was shown to exist as a 11:1 trans:cis mixture of conformers by $^{13}$C NMR analysis (the ratio was estimated from the relative intensities of the resonances at δ41.3 and 48.2 assigned to the Proδ-C atoms of the minor and major conformers, respectively): mp 219-222° C.; [α]$_D$–44.9 (c 1.31 in CH$_2$Cl$_2$); ν$_{max}$ (film)/cm$^{-1}$ 3239, 2927, 1736, 1707, 1617, 1530, 1450, 1403, 1371, 1281, 1241, 1208, 1194, 1165, 1150, 1132, 1089, 1071, 1028, 984, 912, 796, 749, 739 and 699; δ$_H$ (400 MHz, CDCl$_3$)

1.24-2.10 (17H, m, Proα-CH₃, Proβ-H₂, Proγ-H₂ and 5× cyclohexyl-H₂), 3.25-3.48 (1H, br m, Proδ-H$_A$H$_B$), 3.61-3.87 (4H, br m, OCH₃ and Proδ-H$_A$H$_B$), 4.92-5.19 (3H, m, N—H and OCH₂Ph) and 7.35-7.37 (5H, s, Ph); δ$_C$(100 MHz, CDCl₃) 21.26 (CH₂, cyclohexyl-C), 21.33 (CH₂, cyclohexyl-C), 21.7 (CH₃, Proα-CH₃), 24.8 (CH₂, cyclohexyl-C), 25.0 (CH₂, Proγ-C), 29.4* (CH₂, cyclohexyl-C), 29.7* (CH₂, cyclohexyl-C), 31.1 (CH₂, cyclohexyl-C), 31.6 (CH₂, cyclohexyl-C), 31.9* (CH₂, cyclohexyl-C), 32.2* (CH₂, cyclohexyl-C), 32.8* (CH₂, cyclohexyl-C), 37.3 (CH₂, Proβ-C), 41.4* (CH₂, Proβ-C), 48.2 (CH₂, Proδ-C), 52.1 (CH₃, OCH₃), 59.1 (quat., Glyα-C), 66.7 (CH₂, OCH₂Ph), 67.3* (CH₂, OCH₂Ph), 67.4 (quat., Proα-C), 128.0* (CH, Ph), 128.1* (CH, Ph), 128.3 (CH, Ph), 128.5 (CH, Ph), 128.7 (CH, Ph), 136.6 (quat., Ph), 153.7 (quat., NCO₂), 171.0 (quat., Gly-CO) and 174.8 (quat., CO₂CH₃); m/z (EI+) 402.2151 (M⁺. C₂₂H₃₀N₂O₅ requires 402.2155).

(8aS)-Methyl-spiro[cyclohexane-1,3(4H)-tetrahydropyrrolo[1,2-a]pyrazine]-1,4(2H)-dione (Cyclic cyclohlexyl-G-2MeP)

To a solution of amide 15 (40 mg, 0.01 mmol) in methanol (3.3 cm³) was added 10% Pd on activated charcoal (1.6 mg, 0.015 mmol) and the vessel flushed with hydrogen gas. The resulting suspension was stirred vigorously under an atmosphere of hydrogen for 61.5 h, then filtered through a Celite™ pad with methanol (15 cm³). The filtrate was concentrated to dryness under reduced pressure to produce a yellow semi-solid which was purified by reverse-phase C18 flash column chromatography (0-10% CH₃CN/H₂O; gradient elution) to produce cyclic cyclohexyl-G-2MeP (19 mg, 81%) as a white solid: mp 174-177° C.; [α]$_D$ −63.8 (c 1.13 in CH₂Cl₂); ν$_{max}$ (film)/cm⁻¹ 3215, 2925, 2854, 1667, 1646, 1463, 1427, 1276, 1232, 1171, 1085, 1014, 900, 868, 818, 783, 726 and 715; δ$_H$ (400 MHz, CDCl₃) 1.31-1.89 (12H, m, 9× cyclohexyl-H and 8a-CH₃), 1.94-2.15 (4H, m, 7-H₂ and 8-H₂), 2.26 (1H, td, J 13.7 and 4.5, 1× cyclohexyl-H), 3.44-3.51 (1H, m, 6-H$_A$H$_B$), 3.79-3.86 (1H, m, 6-H$_A$H$_B$) and 6.40 (1H, br s, N—H); δ$_C$(100 MHz, CDCl₃) 19.5 (CH₂, 7-C), 20.6 (CH₂, cyclohexyl-C), 20.8 (CH₂, cyclohexyl-C), 24.5 (CH₂, cyclohexyl-C), 25.0 (CH₃, 8a-CH₃), 33.7 (CH₂, cyclohexyl-C), 36.3 (CH₂, 8-C), 36.5 (CH₂, cyclohexyl-C), 44.7 (CH₂, 6-C), 59.5 (quat., 8a-C), 64.0 (quat., 3-C), 168.1 (quat., 4-C) and 171.6 (quat., 1-C); m/z (EI+) 236.15246 (M⁺. C₁₃H₂₀N₂O₂ requires 236.15248).

Example 3

Synthesis of (8aS)-Allyl-hexahydropyrrolo[1,2-a]pyrazine-1,4-dione (Cyclic G-2AllylP)

Scheme 3:

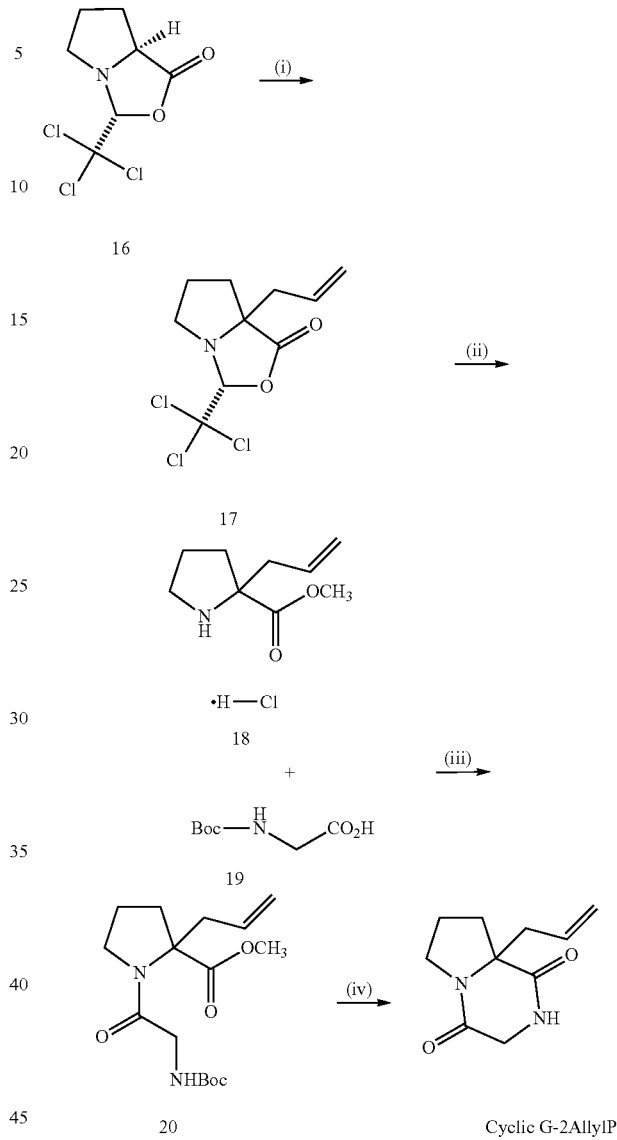

Reagents, conditions and yields: (i) LDA, THF, -78° C., allyl bromide, -78-> -30° C., N₂, 4 h (60%); (ii) acetyl chloride, CH₃OH, reflux, N₂, 24 h (63%); (iii) Et₃N, BoPCl, CH₂Cl₂, RT, N₂, 19.5 h (45%); (iv) TFA, CH₂Cl₂, 1 h, then Et₃N, CH₂Cl₂, 23 h (37%).

(2R,5S)-4-Allyl-2-trichloromethyl-1-aza-3-oxabicyclo[3.3.0]octan-4-one 17 n-BuLi (1.31 M, 9.93 cm³, 13.0 mmol) was added dropwise to a stirred solution of diisopropylamine (1.82 cm³, 13.0 mmol) in dry tetrahydrofuran (20 cm³) at −78° C. under an atmosphere of nitrogen. The solution was stirred for 5 min, warmed to 0° C., stirred for 15 min then added dropwise to a solution of pro-oxazolidinone 16 (2.12 g, 8.68 mmol) in dry tetrahydrofuran (40 cm³) at −78° C. over 20 min and the reaction mixture was stirred for a further 30 min then allyl bromide (2.25 cm³, 26.0 mmol) was added dropwise over 5 min. The solution was warmed slowly to −30° C. over 4 h, quenched with H₂O (30 cm³) and the mixture warmed to room temperature and extracted with chloroform (3×80 cm³). The combined organic extracts were dried (MgSO₄), filtered and evaporated to dryness in vacuo to produce a dark brown semi-solid which was purified by flash column chromatography (10-20% ethyl acetate-hexane; gradient elution) to produce oxazolidinone 17 (1.48 g, 60%) as an orange oil which solidified at 0° C., for which the nmr data were in agreement with that reported in the literature: $\delta_H$ (400 MHz, CDCl$_3$) 1.58-1.92 (2H, m, Proγ-H$_2$), 1.96-2.14 (2H, m, Proβ-H$_2$), 2.50-2.63 (2H, m, Proδ-H$_2$), 3.12-3.23 (2H, m, CH$_2$—CH=CH$_2$), 4.97 (1H, s, NCH), 5.13-5.18 (2H, m, CH=CH$_2$) and 5.82-5.92 (1H, m, CH=CH$_2$); $\delta_C$ (100 MHz, CDCl$_3$) 25.1 (CH$_2$, Proγ-C), 35.1 (CH$_2$, Proβ-C), 41.5 (CH$_2$, Proδ-C), 58.3 (CH$_2$, CH$_2$CH=CH$_2$), 71.2 (quat., Proα-C), 100.4 (quat., CCl$_3$), 102.3 (CH, NCH), 119.8 (CH$_2$, CH$_2$CH=CH$_2$), 131.9 (CH, CH$_2$CH=CH$_2$) and 176.1 (quat., C=O); m/z (CI+) 284.0009 [(M+H)$^+$. C$_{10}$H$_{13}$$^{35}$Cl$_3$NO$_2$ requires 284.0012], 285.9980 [(M+H)$^+$. C$_{10}$H$_{13}$$^{35}$Cl$_2$$^{37}$ClNO$_2$ requires 285.9982], 287.9951 [(M+H)$^+$. C$_{10}$H$_{13}$$^{35}$Cl$^{37}$Cl$_2$NO$_2$ requires 287.9953] and 289.9932 [(M+H)$^+$. C$_{10}$H$_{13}$$^{37}$Cl$_3$NO$_2$ requires 289.9923].

Methyl L-2-allylprolinate hydrochloride 18

An ice-cooled solution of oxazolidinone 17 (0.64 g, 2.24 mmol) in dry methanol (15 cm$^3$) was treated dropwise with a solution of acetyl chloride (0.36 cm$^3$, 5.0 mmol) in methanol (5 cm$^3$). The solution was heated under reflux for 24 h, then cooled and the solvent removed under reduced pressure. The resultant brown oil was dissolved in toluene (40 cm$^3$) and concentrated to dryness to remove residual thionyl chloride and methanol, then purified by flash column chromatography (5-10% CH$_3$OH—CH$_2$Cl$_2$; gradient elution) to afford hydrochloride 18 (0.29 g, 63%) as a green solid for which the NMR data were in agreement with that reported in the literature: $\delta_H$ (300 MHz, CDCl$_3$) 1.72-2.25 (3H, m, Proβ-H$_A$H$_B$ and Proγ-H$_2$), 2.32-2.52 (1H, m, Proβ-H$_A$H$_B$), 2.72-3.10 (2H, m, Proδ-H$_2$), 3.31-3.78 (2H, m, CH$_2$CH=CH$_2$), 3.84 (3H, s, CO$_2$CH$_3$), 5.20-5.33 (2H, m, CH=CH$_2$), 5.75-5.98 (1H, m, CH=CH$_2$) and 8.06 (1H, br s, N—H); m/z (CI+) 170.1183 [(M+H)$^+$. C$_9$H$_{16}$NO$_2$ requires 170.1181].

Methyl-N-tert-butyloxycarbonyl-glycyl-L-2-allylprolinate 20

Dry triethylamine (0.28 cm$^3$, 2.02 mmol) was added dropwise to a solution of hydrochloride 18 (0.13 g, 0.63 mmol) and N-tert-butyloxycarbonyl-glycine 19 (0.14 g, 0.82 mmol) in dry dichloromethane (35 cm$^3$) under an atmosphere of nitrogen at room temperature, and the reaction mixture was stirred for 10 min. Bis(2-oxo-3-oxazolidinyl)phosphinic chloride (BoPCl, 97%) (0.20 g, 0.80 mmol) was added and the solution stirred for 19.5 h, then washed successively with 10% aqueous hydrochloric acid (35 cm$^3$) and saturated aqueous sodium hydrogen carbonate (35 cm$^3$), dried (MgSO$_4$), filtered and evaporated to dryness in vacuo. Purification of the resultant residue by flash column chromatography (40% ethyl acetate-hexane) yielded dipeptide 20 (0.09 g, 45%) as a light yellow oil: $[\alpha]_D$+33.8 (c 0.83 in CH$_2$Cl$_2$); $\nu_{max}$ (film)/cm$^{-1}$ 3419, 3075, 2977, 2930, 2874, 1739, 1715, 1656, 1499, 1434, 1392, 1366, 1332, 1268, 1248, 1212, 1168, 1122, 1051, 1026, 1003, 943, 919, 867, 830, 779, 739, 699 and 679; $\delta_H$ (300 MHz, CDCl$_3$) 1.42 [9H, s, C(CH$_3$)$_3$], 1.93-2.08 (4H, m, Proβ-H$_2$ and Proγ-H$_2$), 2.59-2.67 (1H, m, CH$_A$H$_B$CH=CH$_2$), 3.09-3.16 (1H, m, CH$_A$H$_B$CH=CH$_2$), 3.35-3.44 (1H, m, Proδ-H$_A$H$_B$), 3.56-3.62 (1H, m, Proδ-H$_A$H$_B$), 3.70 (3H, s, OCH$_3$), 3.89 (2H, d, J 4.2, Glyα-H$_2$), 5.06-5.11 (2H, m, CH=CH$_2$), 5.42 (1H, br s, Gly-NH) and 5.58-5.72 (1H, m, CH=CH$_2$); δc (75 MHz, CDCl$_3$) 23.7 (CH$_2$, Proγ-C), 28.3 [CH$_3$, C(CH$_3$)$_3$], 35.0 (CH$_2$, Proβ-C), 37.6 (CH$_2$, CH$_2$CH=CH$_2$), 43.3 (CH$_2$, Glyα-C), 47.5 (CH$_2$, Proδ-C), 52.5 (CH$_3$, OCH$_3$), 68.8 (quat., Proα-C), 79.5 [quat., C(CH$_3$)$_3$], 119.4 (CH$_2$, CH=CH$_2$), 132.9 (CH, CH=CH$_2$), 155.7 (quat., NCO$_2$), 166.9 (quat., Gly-CON) and 173.8 (quat., CO$_2$CH$_3$); m/z (EI+) 326.1845 (M$^+$. C$_{16}$H$_{26}$N$_2$O$_5$ requires 326.1842).

(8aS)-Allyl-hexahydropyrrolo[1,2-a]pyrazine-1,4-dione (Cyclic G-2AllylP)

To a solution of dipeptide 20 (0.09 g, 0.28 mmol) in dichloromethane (9 cm$^3$) at room temperature was added trifluoroacetic acid (1 cm$^3$, 0.013 mmol) dropwise and the reaction mixture was stirred for 1 h under an atmosphere of nitrogen. The solution was evaporated under reduced pressure to give a colorless oil which was dissolved in dichloromethane (10 cm$^3$), dry triethylamine (0.096 cm$^3$, 0.69 mmol) was added and the reaction mixture stirred for 4.5 h, after which further triethylamine (0.096 cm$^3$, 0.69 mmol) was added. The reaction mixture was stirred overnight, concentrated to dryness to give a green oil which was purified by flash column chromatography (10% CH$_3$OH—CH$_2$Cl$_2$) to produce cyclic G-2AllylP (20 mg, 37%) as an off-white solid: mp 106-109° C.; $[\alpha]_D$–102.7 (c 0.95 in CH$_2$Cl$_2$); $\nu_{max}$ (CH$_2$Cl$_2$)/cm$^{-1}$ 3456, 3226, 2920, 1666, 1454, 1325, 1306, 1299, 1210, 1133, 1109, 1028, 1010, 949, 928, 882, 793, 761 and 733; 4' (400 MHz, CDCl$_3$) 1.92-2.01 (2H, m, Proγ-H$_2$), 2.09-2.16 (2H, m, Proβ-H$_2$), 2.39-2.56 (2H, m, CH$_2$CH$_2$=CH$_2$), 3.46-3.53 (1H, m, Proδ-H$_A$H$_B$), 3.78-3.87 (2H, m, Proδ-H$_A$H$_B$ and Glyα-H$_A$H$_B$), 4.09 (1H, d, J 17.2, Glyα-H$_A$H$_B$), 5.16-5.20 (2H, m, CH=CH$_2$), 5.73-5.84 (1H, m, CH=CH$_2$) and 7.17 (1H, br s, N—H); $\delta_C$ (100 MHz, CDCl$_3$) 20.1 (CH$_2$, Proγ-C), 34.1 (CH$_2$, Proβ-C), 41.7 (CH$_2$, CH$_2$CH$_2$=H$_2$), 44.9 (CH$_2$, Proδ-C), 46.4 (CH$_2$, Glyα-C), 67.2 (quat., Proα-C), 120.9 (CH$_2$, CH=CH$_2$), 131.0 (CH, CH=CH$_2$), 163.4 (quat, NCO) and 171.7 (quat., CONH); m/z (EI+) 195.1132 (M$^+$. C$_{10}$H$_{15}$N$_2$O$_2$ requires 195.1134).

Example 4

Synthesis of (8aS)-Methyl-spiro[cyclopentane-1,3 (4H)-tetrahydropyrrolo[1,2-a]pyrazine]-1,4(2H)-dione (Cyclic Cyclopentyl-G-2MeP)

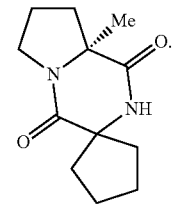

Scheme 3:

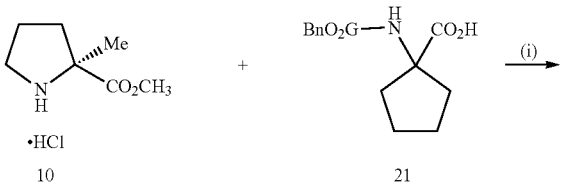

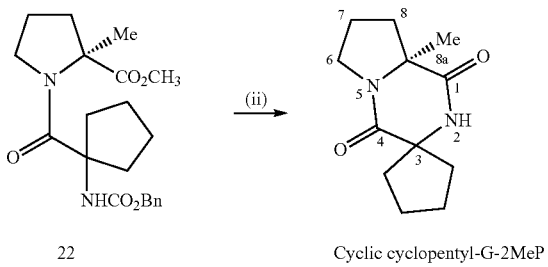

22    Cyclic cyclopentyl-G-2MeP

Reagents, conditions and yields: (i) Et₃N, HOAt, CIP, 1,2-dichloroethane, 83° C., N₂, 19 h (23%); (ii) 10% Pd/C, CH₃OH, RT, 17 h (65%).

N-Benzyloxycarbonyl-1-aminocyclopentane-1-carboxylic acid 21

A solution of benzyl chloroformate (0.290 g, 1.1 mmol) in dioxane (2.5 cm³) was added dropwise to a solution of 1-aminocyclopentanecarboxylic acid (Fluka) (0.2 g, 1.54 mmol) and sodium carbonate (0.490 g, 4.64 mmol) in water (5 cm³) at 0° C. Stirring was continued at room temperature overnight and the reaction mixture washed with ether. The aqueous layer was acidified with 2M hydrochloric acid, extracted with ethyl acetate, dried (Na₂SO₄), filtered and the solvent removed to afford carbamate 21 (0.253 g, 62%) as an oil which solidified on standing. Carbamate 21 was shown to be a 70:30 mixture of conformers by $^1$H NMR analysis (the ratio was estimated from the integration of the resonances at δ 5.31 and 7.29-7.40, assigned to the N—H protons of the major and minor conformers, respectively): mp 70-80° C. (lit.[1] 82-86° C., ethyl acetate, petroleum ether); $δ_H$ (400 MHz; CDCl₃; Me₄Si) 1.83 (4H, br s, 2× cyclopentyl-H₂), 2.04 (2H, br s, cyclopentyl-H₂), 2.20-2.40 (2H, m, cyclopentyl-H₂), 5.13 (2H, br s, OCH₂Ph), 5.31 (0.7H, br s, N—H) and 7.29-7.40 (5.3H, m, Ph and N—H*); $δ_C$ (100 MHz; CDCl₃) 24.6 (CH₂, cyclopentyl-C), 37.5 (CH₂, cyclopentyl-C), 66.0 (quat., cyclopentyl-C), 66.8 (CH₂, OCH₂Ph), 128.0 (CH, Ph), 128.1 (CH, Ph), 128.4 (CH, Ph), 136.1 (quat, Ph), 155.8 (quat., NCO₂) and 179.5 (quat, CO₂H).

Methyl N-benzyloxycarbonyl cyclopentyl-glycyl-L-2-methylprolinate 22

Dry triethylamine (0.19 cm³, 1.4 mmol) was added dropwise to a solution of hydrochloride 10 (78 mg, 0.43 mmol), carboxylic acid 21 (0.15 g, 0.56 mmol) and 1-hydroxy-7-azabenzotriazole (Acros) (15 mg, 0.11 mmol) in dry 1,2-dichloroethane (24 cm³) under an atmosphere of nitrogen at room temperature, and the reaction mixture stirred for 10 min. 2-Chloro-1,3-dimethylimidazolidinium hexafluorophosphate (CIP) (Aldrich) (0.12 g, 0.43 mmol) was added and the resultant solution heated under reflux for 19 h, then washed successively with 10% aqueous hydrochloric acid (30 cm³) and saturated aqueous sodium hydrogen carbonate (30 cm³), dried (MgSO₄), filtered and evaporated to dryness in vacuo. Purification of the resultant residue by flash column chromatography (60% ethyl acetate-hexane) yielded amide 22 (39 mg, 23%) as a white solid. Amide 22 was shown to exist as a 3:1 trans:cis mixture of carbamate conformers by $^{13}$C NMR analysis (the ratio was estimated from the relative intensities of the resonances at δ 154.1 and 155.7 assigned to the carbamate carbonyl-C atoms of the major and minor conformers, respectively): mp 200-203° C.; [α]$_D$ –54.5 (c 1.52 in CH₂Cl₂); $ν_{max}$ (film)/cm$^{-1}$ 3432, 3239, 3042, 2953, 1736, 1712, 1627, 1540, 1455, 1417, 1439, 1374, 1282, 1256, 1216, 1194, 1171, 1156, 1136, 1100, 1081, 1042, 1020, 107, 953, 917, 876, 756 and 701; $δ_H$ (400 MHz, CDCl₃) 1.33-1.53 (3H, br m, Proα-CH₃), 1.62-2.20 (11H, m, Proβ-H₂, Proγ-H₂ and 7× cyclopentyl-H), 2.59-2.71 (1H, br m, 1× cyclopentyl-H), 3.31-3.42 (1H, br m, Proδ-H$_A$H$_B$), 3.58-3.79 (4H, br m, OCH₃ and Proδ-H$_A$H$_B$), 4.92-5.17 (3H, m, N—H and OCH₂Ph) and 7.27-7.42 (5H, s, Ph); $δ_C$ (100 MHz, CDCl₃) 21.7 (CH₃, Proα-CH₃), 24.1* (CH₂, cyclopentyl-C), 24.2 (CH₂, cyclopentyl-C), 24.4 (CH₂, Proγ-C), 24.5 (CH₂, cyclopentyl-C), 36.4 (CH₂, cyclopentyl-C), 37.1 (CH₂, cyclopentyl-C), 37.2* (CH₂, cyclopentyl-C), 37.7 (CH₂, Proβ-C), 38.2* (CH₂, cyclopentyl-C), 48.5 (CH₂, Proδ-C), 52.1 (CH₃, OCH₃), 66.6 (CH₂, OCH₂Ph), 66.9 (quat., Proα-C), 67.2 (quat., Glyα-C), 127.8 (CH, Ph), 128.2 (CH, Ph), 128.4 (CH, Ph), 136.6 (quat, Ph), 154.1 (quat., NCO₂), 155.7* (quat., NCO₂), 170.5 (quat., Gly-CO) and 174.7 (quat., CO₂CH₃); m/z (EI+) 388.1991 (M⁺. C₂₁H₂₈N₂O₅ requires 388.1998).

* denotes resonance assigned to minor conformer.

(8aS)-Methyl-spiro[cyclopentane-1,3(4H)-tetrahydropyrrolo[1,2-a]pyrazine]-1,4(2H)-dione (Cyclic cyclopentyl-G-2MeP)

To a solution of amide 22 (54 mg, 0.14 mmol) in methanol (4.6 cm³) was added 10% Pd on activated charcoal (2.2 mg, 0.021 mmol) and the vessel flushed with hydrogen gas. The resulting suspension was stirred vigorously under an atmosphere of hydrogen for 17 h, then filtered through a Celite™ pad with methanol (15 cm³). The filtrate was concentrated to dryness under reduced pressure to give a yellow semi-solid which was purified by reverse-phase C18 flash column chromatography (0-10% CH₃CN/H₂O; gradient elution) to afford cyclic cyclopentyl-G-2MeP (20 mg, 65%) as a yellow solid: mp 160-163° C.; [α]$_D$ –97.9 (c 1.61 in CH₂Cl₂); $ν_{max}$ (film)/cm$^{-1}$ 3429, 2956, 2928, 2856, 1667, 1643, 1463, 1432, 1373, 1339, 1254, 1224, 1175, 1086, 1048, 976, 835, 774 and 730; $δ_H$ (300 MHz, CDCl₃) 1.47 (3H, br s, 8a-CH₃), 1.56-2.19 (11H, m, 8-H₂, 7-H₂ and 7× cyclopentyl), 2.58-2.67 (1H, br m, 1× cyclopentyl), 3.48-3.56 (1H, m, 6-H$_A$H$_B$), 3.72-3.82 (1H, m, 6-H$_A$H$_B$) and 6.56 (1H, br s, N—H); $δ_C$ (75 MHz, CDCl₃) 19.9 (CH₂, 7-C), 24.6 (CH₂, cyclopentyl), 24.92 (CH₃, 8a-CH₃), 24.93 (CH₂, cyclopentyl), 36.0 (CH₂, 8-C), 38.7 (CH₂, cyclopentyl), 41.9 (CH₂, cyclopentyl), 44.8 (CH₂, 6-C), 64.3 (quat, 8a-C), 66.8 (quat., 3-C), 168.3 (quat., 4-C) and 172.2 (quat., 1-C); m/z (EI+) 222.1369 (M⁺. C₁₂H₁₈N₂O₂ requires 222.1368).

In Vitro and In Vivo Testing

The following pharmacological studies demonstrate neuroprotective features of this invention. They are not intended to be limiting, and other compositions and methods of this invention can be developed without undue experimentation. All of those compositions and methods are considered to be part of this invention. All the following experiments were carried out using protocols developed under guidelines approved by the University of Auckland Animal Ethics Committee.

Example 5

Effects of Cyclic G-2AllylP and Cyclic cyclopentyl-G-2MeP on Cerebellar Cell Explants To determine the effects of cG-2AllylP and cyclic cyclopentyl-G-2MeP on neuronal cells in vitro, a series of studies was carried out using cerebellar explants from adult rats. It vitro systems are suitable for studying neuronal proliferation, neurite growth, formation of nerve bundles and effects of toxins on neural cells, effects that parallel effects observed in vivo. Thus, results of studies using in vitro cerebellar explants are predictive of effects of interventions in vivo.

In a first series of studies, effects of glutamate on cerebellar explants were determined. At physiological concentrations, glutamate is a neurotransmitter in the CNS of mammals, including humans. However, at sufficiently high concentrations, glutamate is neurotoxic, resulting in neuronal cell death. Because glutamate is a naturally occurring neurotransmitter in the CNS of mammals, including humans, and because glutamate neurotoxicity is recognized in the art as reflective of neurotoxicity in general, and including cell death and degeneration, it is a valuable tool useful for identifying and characterizing agents effective in treatment of neurodegeneration and neural cell death.

Materials and Methods

Cover slips were placed into a large Petri dish and washed in 70% alcohol for 5 minutes, then washed with Millipore $H_2O$. The cover slips were air dried, and coated with Poly-D-Lysine (1 mg/ml stock solution in PBS, 90-100 µl) for 2 hours at 34° C.

Extraction of Cerebellar Tissue

Postnatal day 8 Wistar rats were used for the study. The rats were sacrificed and placed in ice for 1 minute, decapitated and the cerebellum removed and placed on ice. Cerebellum tissue was placed in 1 ml of 0.65% glucose-supplemented PBS (10 µl 165% stock D (+)glucose/1 ml PBS) in a large Petri dish, chopped up into smaller sections and triturated with a 1 ml insulin syringe via a 23 G (0.4 mm) needle, and then squirted back into the glucose solution in the large Petri dish. The tissue was sieved through (125 µm pore size gauze) and centrifuged (2 minutes at 60 g) twice to exchange the medium into serum-free BSA-supplemented START V medium (Biochrom, Germany). The second centrifugation step was done with 1 ml of START V medium. The microexplants were reconstituted into 500 µl of START V medium and put on ice.

Cultivation of Cerebellar Cells

Two hours after PDL-coating, the slides were washed with Millipore $H_2O$ and air dried. Each slide was placed into a small Petri dish (diameter: 35 mm) and 40 µl of START V/cell suspension was added. The tissue was incubated for 2 hours at 34° C. (settlement period). START V-medium (1 ml) was then added to the Petri dish and cultivated at 34° C. in the presence of 5% $CO_2$ in air at 100% humidity for 48 hours.

Drug Application

For the study, certain explant cultures were exposed to vehicle (PBS) only. In the first study (Study 1) 10 µl of toxin 1 (L-glutamate-100 mM in Millipore water, final concentration: 1 mM) and 10 µl of toxin 2 (3-nitropropionic acid-50 nM-pH 7-in Millipore water, final concentration: 0.5 mM) was applied simultaneously with the drug to be tested (10 mM stock solution prepared in PBS and diluted to final concentrations between 1-100 nM). In each case, the drugs were left in contact with the explants for the duration of the study.

Methods for Determining Drug Effects

After explants were exposed to drugs for the study period, cells were then rinsed in PBS and then fixed in increasing concentrations of paraformaldehyde (500 µl of 0.4% PFA was applied; then 1.2% PFA; then 3% PFA and finally 4% PFA (each fixation step: 2-3 minutes). Finally, the microexplants were rinsed in PBS.

Neurons in the explants were then evaluated for morphology (presence of neurites) and counted as live cells per microscopic field. Four fields displaying highest cell density were counted per cover slip and the data presented as mean±standard error of the mean (SEM); n=4 each. Statistical significance was evaluated by using the non-paired Student's t-test Results Cyclic G-2-AllylP The results of the study are shown in FIG. 1. Glutamate treatment (1 mM; filled bar) resulted in about an 85% loss of cerebellar neurons having neurites compared to vehicle-treated controls (open bar). In contrast, cG-2AllylP significantly increased the numbers of cells having neurites in a dose-dependent manner when administered simultaneously with glutamate (shaded bars). Treatment with low doses of cG-2AllylP (100 pm to 10 nm) showed a significant decrease in glutamate-induced neurotoxicity.

Cyclic cyclopentyl-G-2MeP

Figure 2:
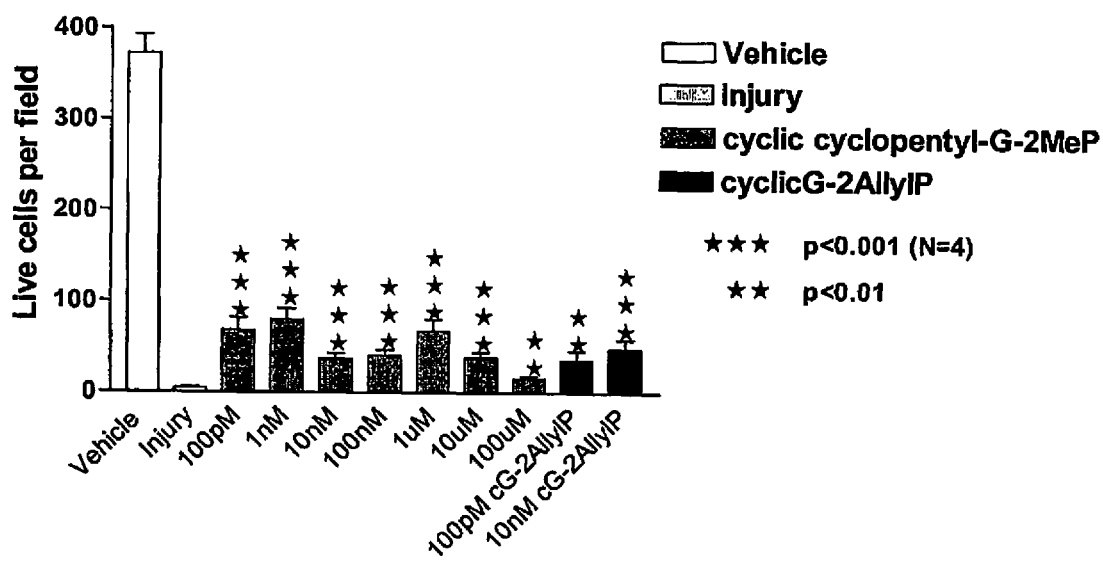
FIG. 2 is a graph showing effects of cyclic cyclopentylG-2MeP on neuronal survival in animals following excitotoxic oxidative stress.

The results of the study are shown in FIG. 2. Cyclic cyclopentyl-G-2MeP significantly increased the number of cells having neurites when simultaneously administered with glutamate (light shaded bars). Treatment with low doses of cyclic cyclopentyl-G-2MeP showed a significant decrease in glutamate-induced neurotoxicity.

Conclusions

Both cG-2AllylP and cyclic cyclopentyl-G-2MeP independently decreased or prevented glutamate-induced neurotoxicity, indicating that both drugs are neuroprotective and can be used to inhibit neuronal degeneration or cell death.

Example 6

Effects of cG-2AllylP on Hypoxic-Ischemic Injury I

Materials and Methods

To determine whether cG-2AllylP might prevent neuronal injury in response to stroke, cardiac arterial bypass graft surgery (CABG) or other hypoxic insults, a series of studies were carried out in rats that had been exposed to hypoxic-ischemic injury (HI). Adult rats (Wistar, 280-310 g, male) were used. The modified Levine model preparation and experimental procedures were used (Rice et al., 1981, *Ann. Neurol.*: 9: 131-141; Guan et al J., 1993, *Cereb. Blood Flow Metab.*: 13(4): 609-16). These procedures in brief, consist of an HI injury induced by unilateral carotid artery ligation followed by inhalational asphyxia in the animals with an implanted lateral ventricular cannula. A guide cannula was stereotaxically placed on the top of the dura 1.5 mm to the right of the mid-line and 7.5 mm anterior to the interaural zero plane under halothane anaesthesia. The right carotid artery was double ligated two days after the cannulation. After 1 hour recovery from the anaesthesia, each of the rats were placed in an incubator where the humidity (90±5%) and temperature (31°±0.5° C.) were controlled for another hour, then exposed to hypoxia (6% oxygen) for 10 min. The animals were kept in the incubator for an additional 2 hours before treatment.

Nine pairs of rats were treated intracerebral ventricularly (icv) with either cG-2AllylP (2 ng) or its vehicle (normal saline) 2 hours after hypoxic-ischemic insult. Rats in each group were simultaneously infused with cG-2AllylP or its vehicle under light anaesthesia (1.5% halothane) 2 hours after the insult. A total volume of 20 µl was infused (icv) over 20 minutes by a micro-infusion pump.

Histological examination was performed on rats 5 days after the hypoxic-ischemic injury. The rats were killed with an overdose of sodium pentobarbital and were perfused transcardially with normal saline followed by 10% formalin. The brains were kept in the same fixative for a minimum of 2 days before being processed using a standard paraffin imbedding procedure.

Coronal sections 8 μm in thickness were cut from the striatum, cerebral cortex and hippocampus and were stained with thionin and acid fuchsin. The histological outcome was assessed at three levels: (1) the mid level of the striatum, (2) where the completed hippocampus first appeared and (3) the level where the ventral horn of the hippocampus just appears. The severity of tissue damage was scored in the striatum, cortex and the CA1-2, CA3, CA4 and dentate gyrus of the hippocampus. Tissue damage was identified as neuronal loss (acidophilic (red) cytoplasm and contracted nuclei), pan-necrosis and cellular reactions. Tissue damage was scored using the following scoring system: 0: tissue showed no tissue damage, 1: <5% tissue was damaged, 2: <50% tissue was damaged, 3: >50% tissue was damaged and 4: >95% tissue was damaged.

Results and Conclusion

Figure 3:
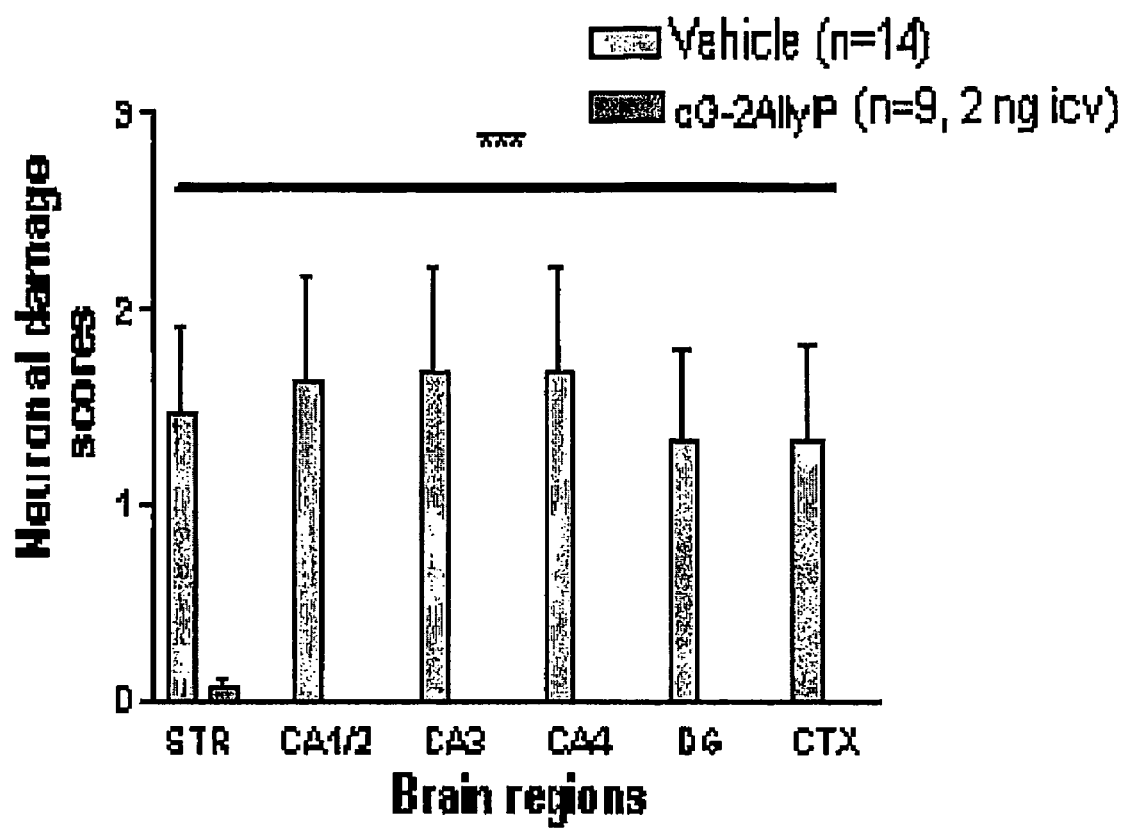
FIG. 3 is a graph showing the neuroprotective effects of cyclic G-2allylP in animals subjected to global brain ischaemia.

The results of this study are shown in FIG. 3. FIG. 3 shows that hypoxic-ischemic injury (left bars of each set) resulted in significant damage scores in each of the areas of the brain studied. FIG. 3 also shows that central administration of a relatively low dose of cG-2AllylP (right bars of each set; 2 ng) significantly reduced the tissue damage in each brain region examined compared to the vehicle treated group (p<0.001).

It can be seen that cG-2AllylP can be neuroprotective against neural damage caused by hypoxic-ischemic injury, even when administered after hypoxic-ischemic injury. This surprising finding indicates that cG-2AllylP is a useful agent to treat a variety of conditions characterized by neural degeneration or cell death.

Example 7

Effects of cG-2AllylP on Hypoxic-Ischemic Injury II

Materials and Methods

Materials and methods described in Example 6 were used and the number of treatment groups was increased. Rats were divided into 5 treatment groups treated intracerebral ventricularly (icv) with one of 4 doses of cG-2AllylP or with its vehicle (normal saline) 2 hours after hypoxic-ischemic insult (1: n=10, 2 ng; 2: n=9, 4 ng; 3: n=9, 20 ng; 4: n=10, 100 ng; and 5: n=9, vehicle).

Figure 4:
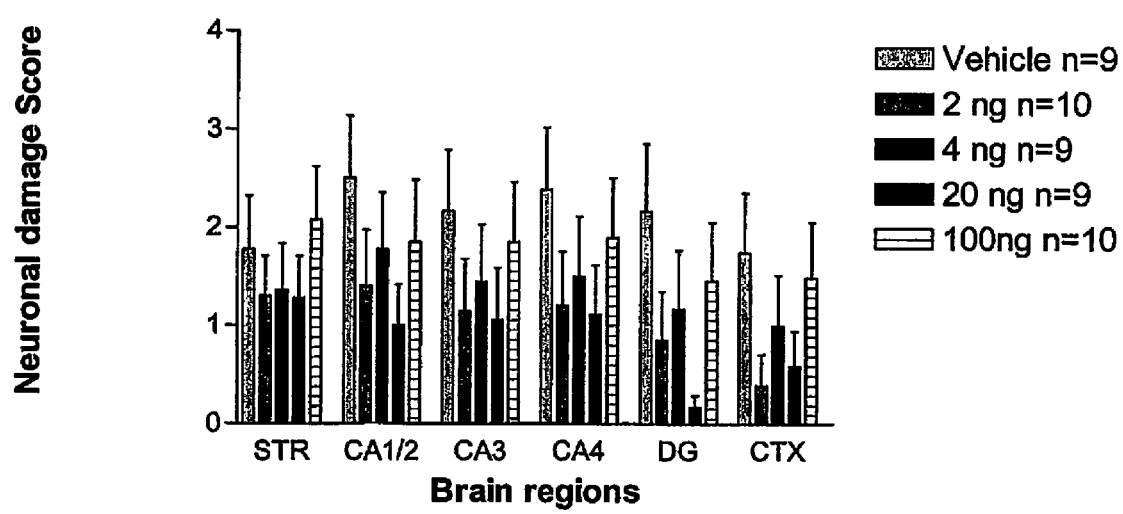
FIG. 4 is a graph showing effects of different doses of cyclic G-2allylP on neuroprotection in animals subjected to global brain ischaemia.

FIG. 4 shows hypoxia alone (vehicle) produces neuronal damage scores in all areas of the brain studied. In animals treated with cG-2allylP, hypoxia had less effect, even though the agent was administered after the hypoxic/ischemic injury. The neuroprotective effect was observed for all doses of cG-2allylP, except for the highest dose (100 ng) administered to the striatum. However, in all other sites and with all other doses, cG-2allylP lessened the neural damage effects of hypoxia/ischemia. Moreover, cG-2allylP had an increased efficacy in brain regions that experienced progressive injury associated with delayed cell death, such as that associated with apoptosis. In brain regions such as the dentate gyrus and the cerebral cortex, that are more resistant to HI injury, the progression of injury is known to be slower and more severe than in the brain regions that are more sensitive to FE injury such as the striatum and the CA1-2, CA3 and CA4 subregions of the hippocampus. This result shows that cG-2allylP can be beneficial in treatment of chronic neurological disorders.

The descriptions and examples provided herein are for purposes of illustration only. The scope of this invention to is not intended to be limited to the described embodiments. Other embodiments incorporating elements of the invention can be practiced without undue experimentation by persons of ordinary skill in the art. All such embodiments are therefore considered to be part of this invention. All references cited herein are incorporated fully by reference.

What is claimed is:

1. A compound having the formula:

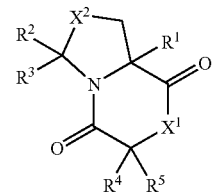

or a pharmaceutically acceptable salt or thereof, where
$X^1$ is NH;
$X^2$ is $CH_2$;
$R^1$ is allyl,
$R^2$, and $R^3$ are independently selected from the group consisting of —H, —OR', —SR', —NR'R', —$NO_2$, —CN, —C(O)OR', —C(O)NR'R', —C(NR')NR'R', trihalomethyl, halogen, alkyl, heteroalkyl, alkenyl, alkynyl, aryl, heteroaryl, arylalkyl, and heteroarylalkyl; each R' is independently selected from the group consisting of —H, alkyl, heteroalkyl, alkenyl, alkynyl, aryl, arylalkyl, heteroaryl and heteroarylalkyl;
$R^4$ and $R^5$ are H;
and optionally, wherein $R^2$ and $R^3$ taken together are —$CH_2$—$(CH_2)_n$—$CH_2$— where n is an integer from 0-6.

2. The compound of claim 1 where, $R^2=R^3=H$.

3. A pharmaceutical composition comprising a compound of claim 1 and a pharmaceutically acceptable excipient.

* * * * *

UNITED STATES PATENT AND TRADEMARK OFFICE
CERTIFICATE OF CORRECTION

PATENT NO. : 8,067,425 B2
APPLICATION NO. : 10/570395
DATED : November 29, 2011
INVENTOR(S) : Margaret Brimble et al.

Page 1 of 1

It is certified that error appears in the above-identified patent and that said Letters Patent is hereby corrected as shown below:

In the Claims:

Column 34, Line 39, Claim 1: Please insert --C(O)R'-- before "C(O)OR"

Signed and Sealed this
Sixteenth Day of July, 2013

Teresa Stanek Rea
*Acting Director of the United States Patent and Trademark Office*